(12) United States Patent
Yamamoto et al.

(10) Patent No.: US 7,553,796 B2
(45) Date of Patent: *Jun. 30, 2009

(54) PHENOL COMPOUND, REVERSIBLE THERMOSENSITIVE RECORDING MEDIUM, REVERSIBLE THERMOSENSITIVE RECORDING LABEL, REVERSIBLE THERMOSENSITIVE RECORDING MEMBER, IMAGE-PROCESSING APPARATUS AND IMAGE-PROCESSING METHOD

(75) Inventors: Satoshi Yamamoto, Odawara (JP); Kyoji Tsutsui, Mishima (JP); Hiromi Furuya, Shizuoka (JP); Kyohji Okada, Fuji (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/886,200

(22) PCT Filed: Mar. 16, 2006

(86) PCT No.: PCT/JP2006/305767
§ 371 (c)(1),
(2), (4) Date: May 14, 2008

(87) PCT Pub. No.: WO2006/098507
PCT Pub. Date: Sep. 21, 2006

(65) Prior Publication Data
US 2008/0242539 A1    Oct. 2, 2008

(30) Foreign Application Priority Data
Mar. 17, 2005  (JP) .............................. 2005-076428

(51) Int. Cl.
*B41M 5/333*  (2006.01)

(52) U.S. Cl. ................ 503/201; 346/135.1; 503/214; 503/216; 503/226; 564/443

(58) Field of Classification Search ................ None
See application file for complete search history.

(56) References Cited

U.S. PATENT DOCUMENTS

| 5,395,815 A | 3/1995 | Ikeda et al. |
| 5,710,094 A | 1/1998 | Minami et al. |
| 6,001,518 A | 12/1999 | Ohsawa et al. |

FOREIGN PATENT DOCUMENTS
EP    0574879 A1    12/1993

(Continued)

OTHER PUBLICATIONS

Feb. 24, 2009 European search report in connection with a counterpart European patent Application No. 06 72 9734.

*Primary Examiner*—Bruce H Hess
(74) *Attorney, Agent, or Firm*—Cooper & Dunham, LLP

(57) ABSTRACT

The present invention provides a reversible thermosensitive recording medium including a support and a thermosensitive recording layer thereon, in which the thermosensitive recording layer contains an electron-donating coloring compound and an electron-accepting compound, and the thermosensitive recording layer is capable of forming a relatively developed condition and a relatively erased condition depending on at least one of the difference of heating temperatures and the difference of cooling rates following to heating, and in which the electron-accepting compound contains a phenol compound expressed by General Formula (1):

General Formula (1)

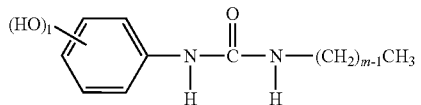

where, in the General Formula (1), "l" represents an integer of 1 to 3 and "m" represents an integer of 23 or more.

23 Claims, 14 Drawing Sheets

FOREIGN PATENT DOCUMENTS

| | | |
|---|---|---|
| EP | 0709225 A1 | 5/1996 |
| EP | 0870624 A1 | 10/1998 |
| JP | 5-124360 | 5/1993 |
| JP | 6-210954 | 8/1994 |
| JP | 10-67177 | 3/1998 |
| JP | 10-95175 | 4/1998 |
| JP | 2000-141901 | 5/2000 |
| JP | 2001-105739 | 4/2001 |
| JP | 2001-121820 | 5/2001 |
| JP | 2001-162936 | 6/2001 |
| JP | 2002-187362 | 7/2002 |
| JP | 2002-337456 | 11/2002 |
| JP | 2004-1427 | 1/2004 |
| JP | 2005-1127 | 1/2005 |

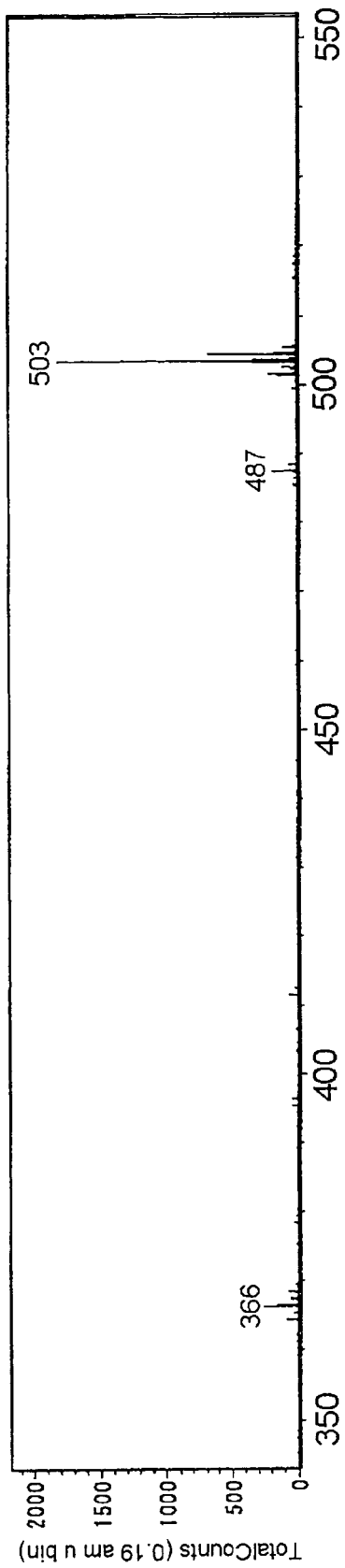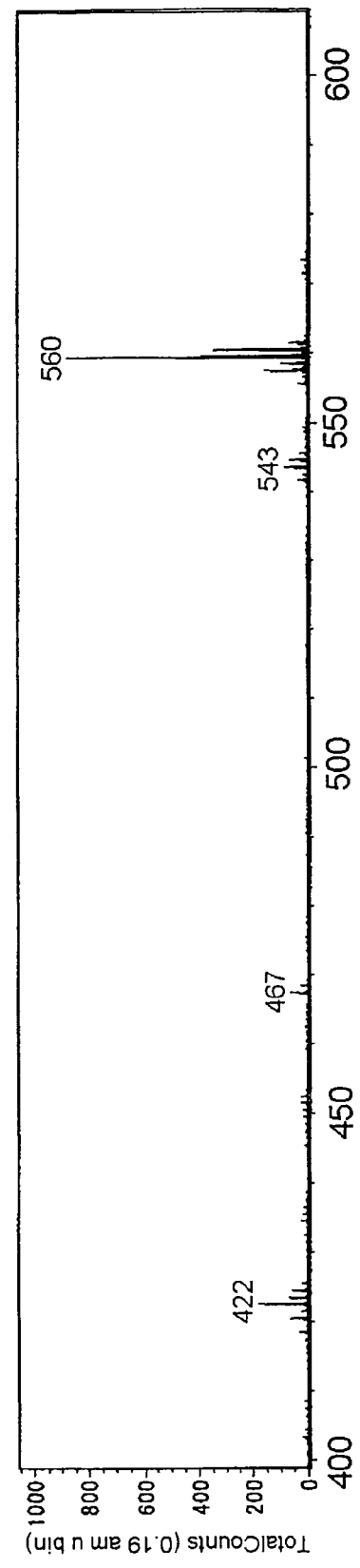

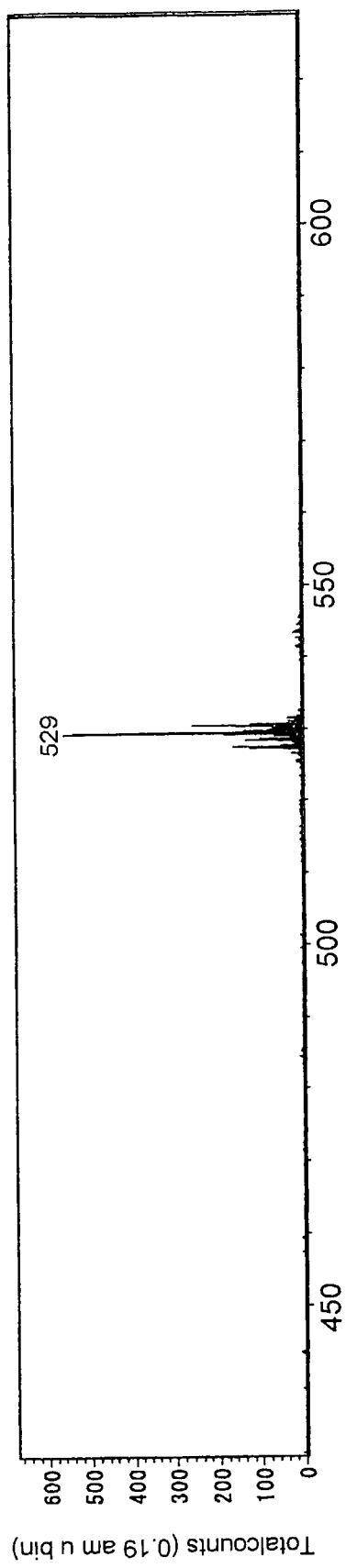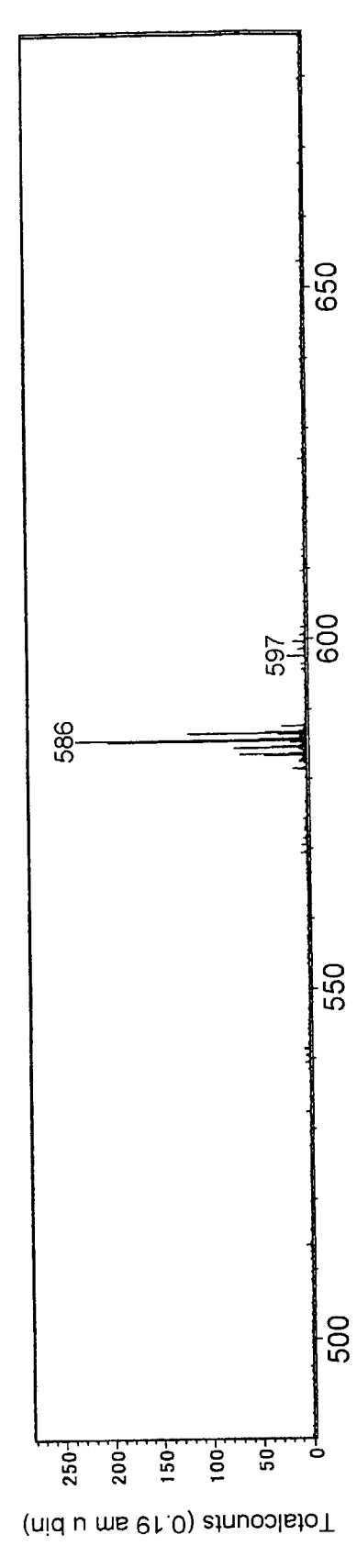

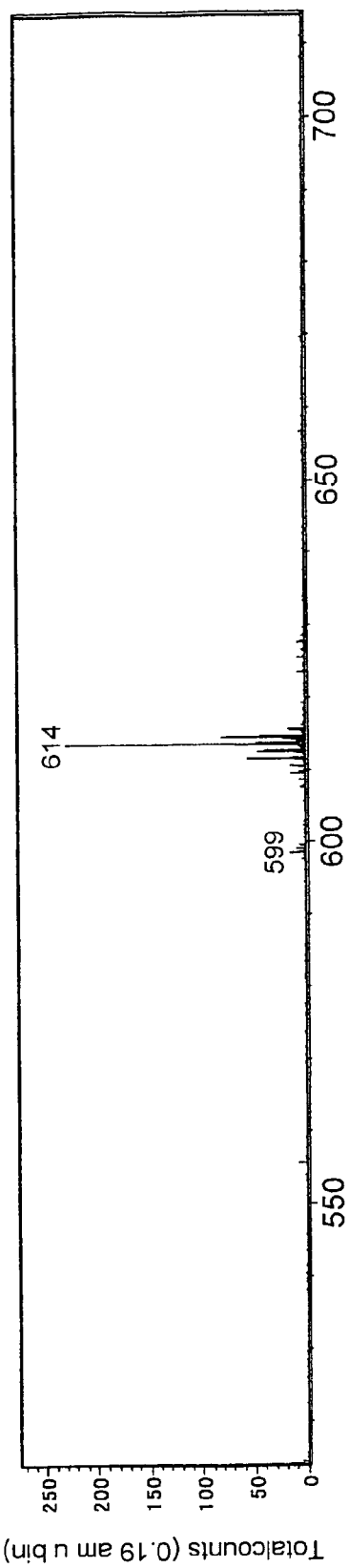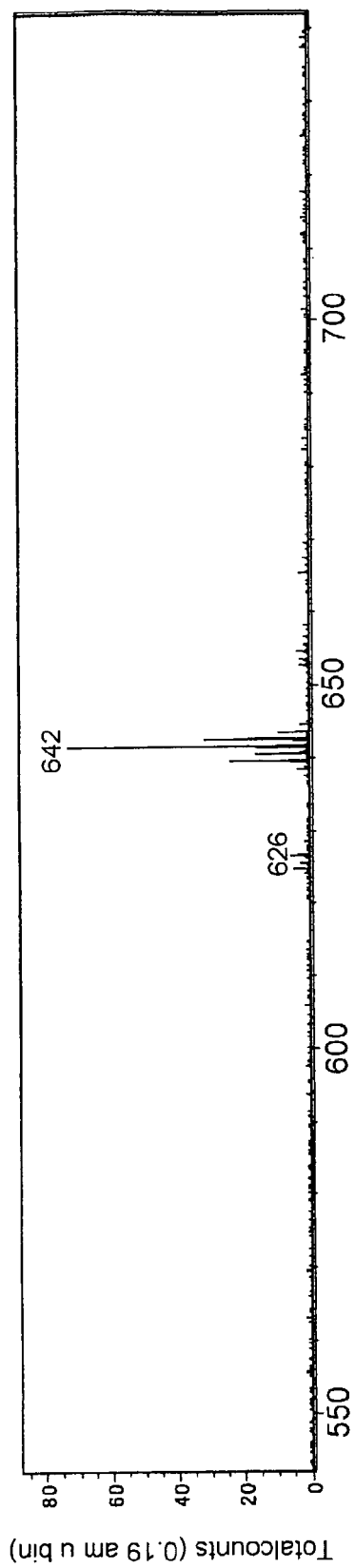

PHENOL COMPOUND, REVERSIBLE THERMOSENSITIVE RECORDING MEDIUM, REVERSIBLE THERMOSENSITIVE RECORDING LABEL, REVERSIBLE THERMOSENSITIVE RECORDING MEMBER, IMAGE-PROCESSING APPARATUS AND IMAGE-PROCESSING METHOD

TECHNICAL FIELD

This disclosure relates to a new phenol compound useful as a color developer of a reversible thermosensitive recording medium, a reversible thermosensitive recording medium in which color images may be formed and erased reversibly based on color-developing reactions between electron-donating coloring compounds and electron-accepting compounds by controlling applied thermal energies, and also relates to a reversible thermosensitive recording label, a reversible thermosensitive recording member, an image-processing apparatus and an image-processing method which employ the reversible thermosensitive recording medium respectively.

BACKGROUND ART

Thermosensitive recording media which utilize reactions between electron-donating coloring compounds (hereinafter, sometimes referred as "coloring agent" or "leuco dye") and electron-accepting compounds (hereinafter, sometimes referred as "color developer") are well-known and have been broadly utilized as output papers of facsimiles, word processors and scientific instrumentation apparatuses, with an advance of office automation, and nowadays in magnetic thermosensitive cards such as a pre-paid card and point card.

From an environmental issue, these conventional recording media in practical use are under pressure to review their use and are required to be recycled, and to be used in fewer amounts; however, recorded images cannot be erased, and thus cannot be used repeatedly. In addition, new information is written only to non-recorded portion, and therefore the total areas capable of being recorded are limited. Thus, under the current situation, the amount of information to be recorded is reduced or a new card is issued when area to be recorded is fully occupied. Because of the backdrop of waste problem or problem of deforestation, development of reversible thermosensitive recording medium which is rewritable many times had been desired.

From theses demands, various kinds of reversible thermosensitive recording media have been disclosed. For example, Patent Literatures 1 and 2 disclose a reversible thermosensitive recording medium which is a kind of those using polymer, in which physical change, i.e., transparent and white opaque is utilized. Alternatively, there has been a proposed reversible thermosensitive recording medium which is a kind of those using a dye, in which chemical change is newly utilized. Specifically, for example, gallic acid is used in combination with phloroglucinol as a color developer (see Patent Literature 3). Such compounds as phenolphthalein and thymolphthalein are used as a color developer (see Patent Literature 4). Homogeneous mixed solution composed of coloring agent, color developer, and carboxylic acid ester are contained in a recording layer (see Patent Literatures 5, 6, and 7). Ascorbic acid derivatives are used as a color developer (see Patent Literature 8). Salts of bis (hydroxyphenyl) acetic acid or gallic acid and higher aliphatic amine are used as a color developer (see Patent Literatures 9 and 10).

Further, Patent Literature 11 discloses a reversible thermosensitive coloring composition and thermosensitive recording medium. In the reversible thermosensitive coloring composition, an organic phosphorus compound, fatty carbonyl acid compound, or phenol compound each containing a long-chain aliphatic hydrocarbon group as a developing agent is combined with a leuco dye as a coloring agent, thereby allowing coloring and erasing easily depending on the heating and cooling condition. The developed condition and erased condition can be stably maintained at normal temperature and in addition, developing and erasing can be repeated. And then, Patent Literatures 12 and 13 disclose use of a phenol compound containing a long-chain fatty hydrocarbon group which compound has a specific structure.

In the recording medium where these materials are employed, however, there were such problems that the erasing rate is slow and taking much time to rewrite; erasing is inadequate, or thermal stability of color images is low.

Therefore, Patent Literature 14 discloses a recording medium in which a specific phenol compound is used, thereby allowing high contrast between developed condition and erased condition, high-speed erasing, and excellent stability of coloring of an image part. In this recording medium in which the phenol compound is used, color images can be erased by means of a heating member such as a hot stamp, heat roller, or ceramic heater. Therefore, the reversible thermosensitive recording medium is suitable for practical use.

However, many of the compounds exemplified in the above-mentioned Patent Literature 14 have high melting point, which requires heating to high temperature during color developing and erasing and thus requires application of high energy.

As a result, some problems arise. Specifically, since pulse is required to be applied for a long time during recording, writing speed is slow, and further high temperature causes large damage to the recording medium, inviting occurrence of blowing trace. In addition, the power supply of the recording apparatus becomes large, resulting in larger rewriting apparatus.

Further, as the phenol compound described in the above-mentioned Patent Literature 12, those having relatively low melting point also have been proposed; however, the recording media in which these compounds were employed exhibits satisfactory coloring sensitivity, but the preservability of the images is not satisfactory and thus the recording media had low practical use. Moreover, a phenol compound containing a long-chain alkyl urea having carbon number 22 is disclosed in Patent Literature 12. The recording media utilizing such phenol compound excel in coloring sensitivity, color optical density and erasing optical density, however, storage stability in image parts is not satisfactory and image density is significantly lowered at a 60° C. storage test normally required for these recording media therefore they are not practical for use.

Moreover, a specific phenol compound having a long-chain alkyl group of carbon number 23 or more is disclosed in Patent Literatures 15 and 16. However, there are problems in the recording media using these compounds such as low coloring sensitivity, inappropriate storage stability of image parts or being unfavorable for high-speed erasing because of slow erasing speed and therefore, they are not practical for use.

[Patent Literature 1] Japanese Patent Application Laid-Open (JP-A) No. 63-107584
[Patent Literature 2] JP-A No. 04-78573
[Patent Literature 3] JP-A No. 60-193691
[Patent Literature 4] JP-A No. 61-237684
[Patent Literature 5] JP-A No. 62-138556

[Patent Literature 6] JP-A No. 62-138568
[Patent Literature 7] JP-A No. 62-140881
[Patent Literature 8] JP-A No. 63-173684
[Patent Literature 9] JP-A No. 02-188293
[Patent Literature 10] JP-A No. 02-188294
[Patent Literature 11] JP-A No. 05-124360
[Patent Literature 12] JP-A No. 06-210954
[Patent Literature 13] JP-A No. 10-95175
[Patent Literature 14] JP-A No. 10-67177
[Patent Literature 15] JP-A No. 2000-141901
[Patent Literature 16] JP-A No. 2005-1127

SUMMARY

In an aspect of this disclosure, there are provided a new phenol compound useful as a color developer of a reversible thermosensitive recording medium and a reversible thermosensitive recording medium which exhibits satisfactory coloring sensitivity and excellent heat resistance and preservability of image parts, and reversible thermosensitive recording label, reversible thermosensitive recording member, image-processing apparatus and image-processing method which employ the reversible thermosensitive recording medium respectively.

The present inventors considered that in reversible color developing and erasing phenomenon of the composition which contains the coloring agent and color developer, balance between ability of the color developer having a long-chain aliphatic group to develop the coloring agent and the cohesive property between molecules, is important. Further, they considered that in order to increase coloring sensitivity, the color developer is required to have a lower melting point. As a result of designing compounds with a variety of structures, they have found that use of a specific phenol compound having a long-chain alkyl group of carbon number 23 or more and urea group as color developer can achieve high coloring sensitivity and preservability and high-speed erasing ability of image parts which had not been achieved by known compounds in the past and can solve the above-mentioned problems.

The means to settle above issues are as follow.

<1> A reversible thermosensitive recording medium containing a support and a thermosensitive recording layer thereon, wherein the thermosensitive recording layer contains an electron-donating coloring compound and an electron-accepting compound, the thermosensitive recording layer is capable of forming a relatively developed condition and a relatively erased condition depending on at least one of the difference of heating temperatures and the difference of cooling rates following to heating, and the electron-accepting compound contains a phenol compound expressed by following General Formula (1):

General Formula (1)

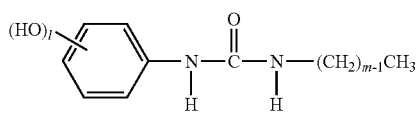

where, in the General Formula (1), "l" represents an integer of 1 to 3 and "m" represents an integer of 23 or more.

<2> The reversible thermosensitive recording medium as stated in above <1>, wherein "m" represents an integer of 23 to 40.

<3> The reversible thermosensitive recording medium as stated in any one of above <1> and <2>, wherein the thermosensitive recording layer contains a crosslinked resin.

<4> The reversible thermosensitive recording medium as stated in above <3>, wherein the crosslinked resin has a hydroxyl value of 70 KO H mg/g or more.

<5> The reversible thermosensitive recording medium as stated in any one of above <3> and <4>, wherein the crosslinked resin is an acrylpolyol resin.

<6> The reversible thermosensitive recording medium as stated in any one of above <3> to <5>, wherein the crosslinked resin is crosslinked with an isocyanate compound.

<7> The reversible thermosensitive recording medium as stated in any one of above <1> to <6>, wherein the electron-donating coloring compound is a leuco dye.

<8> The reversible thermosensitive recording medium as stated in any one of above <1> to <7>, wherein the reversible thermosensitive recording medium contains a protective layer on the thermosensitive recording layer and the protective layer contains a crosslinked resin.

<9> The reversible thermosensitive recording medium as stated in above <8>, wherein the protective layer contains an ultraviolet-absorbing polymer.

<10> The reversible thermosensitive recording medium as stated in any one of above <8> and <9>, wherein the protective layer contains ultraviolet-absorbing inorganic fine particles.

<11> The reversible thermosensitive recording medium as stated in any one of above <1> to <10>, wherein the reversible thermosensitive recording medium is formed into one of a card-like, label-like, sheet-like and roll-like configurations.

<12> A reversible thermosensitive recording label containing the reversible thermosensitive recording medium as stated in any one of above <1> to <11> and one of an adhesive layer and a tacky layer, wherein one of the adhesive layer and the tacky layer is disposed on a surface of the reversible thermosensitive recording medium opposite to the surface on which an image is formed.

<13> A reversible thermosensitive recording member containing an information-memorizing part and a reversible displaying part, wherein the reversible displaying part contains the reversible thermosensitive recording medium as stated in any one of above <1> to <11>.

<14> The reversible thermosensitive recording member as stated in above <13>, wherein the information-memorizing part and the reversible displaying part are integrated.

<15> The reversible thermosensitive recording member as stated in any one of above <13> and <14>, wherein the information-memorizing part is selected from a magnetic thermosensitive layer, a magnetic stripe, an IC memory, an optical memory, a hologram, a RF-ID tag card, a disc, a disc cartridge and a tape cassette.

<16> An image-processing apparatus containing one of an image-forming unit and an image-erasing unit, wherein images are formed on a reversible thermosensitive recording medium by heating the reversible thermosensitive recording medium in the image-forming unit, images are erased from the reversible thermosensitive recording medium by heating the reversible thermosensitive recording medium in the image-erasing unit, and the reversible thermosensitive recording medium is the reversible thermosensitive recording medium as stated in any one of above <1> to <11>.

<17> The image-processing apparatus as stated in above <16>, wherein the image-forming unit is one of a thermal head and a laser irradiation apparatus.

<18> The image-processing apparatus as stated in any one of above <16> and <17>, wherein the image-erasing unit is one selected from a thermal head, a ceramic heater, a heat roll, a hot stamp, a heat block and a laser irradiation apparatus.

<19> An image-processing method containing one of forming images on a reversible thermosensitive recording medium by heating the reversible thermosensitive recording medium, and erasing images from a reversible thermosensitive recording medium by heating the reversible thermosensitive recording medium, wherein the reversible thermosensitive recording medium is the reversible thermosensitive recording medium as stated in any one of above <1> to <11>.

<20> The image-processing method as stated in above <19>, wherein the image forming is carried out by means of one selected from a thermal head and a laser irradiation apparatus.

<21> The image-processing method as stated in any one of above <19> and <20>, wherein the image erasing is carried out by means of one selected from a thermal head, a ceramic heater, a heat roll, a hot stamp, a heat block and a laser irradiation apparatus.

<22> The image-processing method as stated in any one of above <19> to <21>, wherein the image-processing method contains new image forming while images are being erased by means of a thermal head.

<23> A phenol compound containing a structure expressed by following General Formula (2):

General Formula (2)

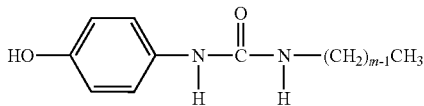

where, in the General Formula (2), "m" represents an integer of 23 to 29.

BRIEF DESCRIPTION OF DRAWINGS

FIG. 6C shows a positive ion peak profile of a synthesized compound in Example 3 used for the present invention obtained by use of a time-of-flight secondary ion mass spectrometer.

FIG. 6D shows a positive ion peak profile of a synthesized compound in Example 4 used for the present invention obtained by use of a time-of-flight secondary ion mass spectrometer.

FIG. 7E shows a negative ion peak profile of a synthesized compound in Example 5 used for the present invention obtained by use of a time-of-flight secondary ion mass spectrometer.

FIG. 7F shows a negative ion peak profile of a synthesized compound in Synthetic Example 1 used for the present invention obtained by use of a time-of-flight secondary ion mass spectrometer.

FIG. 7G shows a negative ion peak profile of a synthesized compound in Synthetic Example 2 used for the present invention obtained by use of a time-of-flight secondary ion mass spectrometer.

FIG. 7H shows a negative ion peak profile of a synthesized compound in Synthetic Example 3 used for the present invention obtained by use of a time-of-flight secondary ion mass spectrometer.

BEST MODE FOR CARRYING OUT THE INVENTION (Phenol Compound and Reversible Thermosensitive Recording Medium)

The phenol compound according to the present invention is a new phenol compound expressed by following General Formula (2):

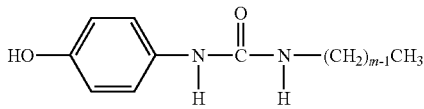

General Formula (2)

where, in the General Formula (2), "m" represents an integer of 23 to 29.

The reversible thermosensitive recording medium according to the present invention contains a support, at least a thermosensitive recording layer on the support and other layers as necessary.

The thermosensitive recording layer contains a phenol compound expressed by following General Formula (1):

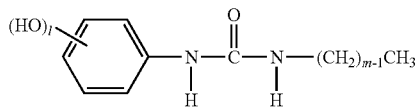

General Formula (1)

where, in the General Formula (1), "l" represents an integer of 1 to 3 and "m" represents an integer of 23 or more.

The reversible thermosensitive recording medium according to the present invention in which the phenol compound is used can form a relatively developed condition and a relatively erased condition depending on the heating temperatures and/or cooling rates following to heating. The essential color developing and erasing phenomenon will be described below.

Figure 1:
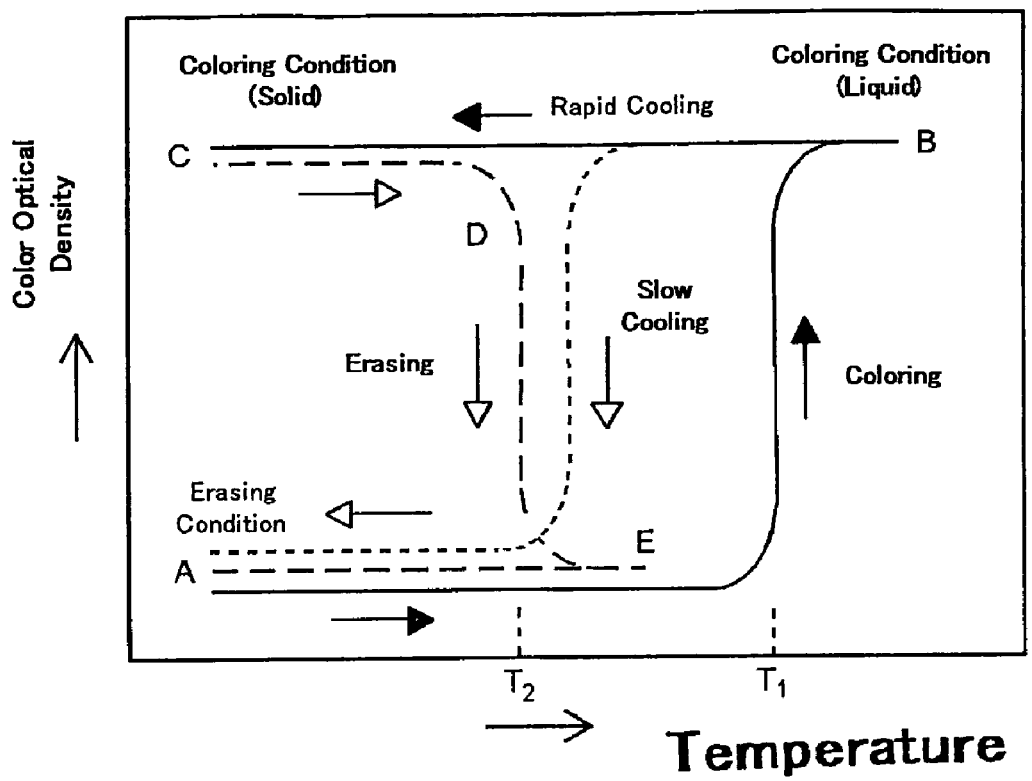
FIG. 1 schematically shows the color developing and erasing property in the reversible thermosensitive coloring composition according to the present invention.

Here, FIG. 1 shows the relation between the color optical density and the temperature in the reversible thermosensitive recording medium. When the recording medium is heated from the initial erased condition (A), a leuco dye and color developer are melted at the temperature $T_1$ at which the melting begins, and then the recording medium comes to the melted and developed condition (B), through an occurrence of developing. When cooled rapidly from the melted and developed condition (B), it may be cooled to the room temperature while maintaining the developed condition, thereby a fixed and developed condition (C) emerges. Whether or not the developed condition emerges depends on the cooling rate from the melted condition, and when cooled slowly, the erasing appears during a temperature decreasing process, that is, the initial erased condition (A) or lower density than rapid cooling (C) emerges. On the other hand, when heated again from rapidly cooled coloring condition (C), erasing occurs at a lower temperature $T_2$ than the developing temperature (D to E); when cooled from this temperature, resulting in the initial erased condition (A). Actual developing and erasing temperatures may be selected depending on the application since these temperatures vary with the utilized coloring agent and color developer. Further, the color optical density at the melting condition and the color optical density after the rapid cooling may not necessarily coincide and may differ significantly in some cases.

In the reversible thermosensitive recording medium of the present invention, the coloring condition (C) obtained through rapid cooling from the melted condition is a condition in which the coloring agent and color developer are blended such that they may react through molecular contact, and the coloring condition is often solid state. In the condition, the coloring agent and color developer are coagulated to represent a coloring condition. It is believed that the formation of the coagulated condition makes the coloring condition stable. On the other hand, in the erased condition, the coloring agent and color developer are in phase separation. It is believed that the molecules of at least one of the compounds assemble to form domains or crystals in the separated condition, and that the coloring agent and color developer are separated and stabilized through the coagulation or crystallization. In the present invention, in many cases, the phase separation of the coloring agent and the color developer and also the crystallization of the color developer cause the erasion more perfectly. In the erasion due to slower cooling from the melted condition as well as the erasion due to the heating from the coloring condition as shown in FIG. 1, the coagulated structures are altered depending on the temperatures, resulting in the phase separation and/or crystallization of the color developer.

The color developer contains a phenol group which is a coloring region and hydrogen bond association and long-chain aliphatic hydrocarbon group dominating the structure as an important platform for providing coloring and erasing abilities. It has been mainly focused on the balance between the phenol group which is a coloring region and hydrogen-bonding association dominating the structure. Because it was considered that the stability in coloring condition increases as coagulated structure of color developer and coloring agent are more stabilized. Consequently, introducing one and/or two or more hydrocarbon-bonding association in the molecular structure of color developers has been investigated. However, the melting point of color developers becomes high for stronger hydrogen bond of color developer molecules or increased number of hydrogen bond and coloring starting temperature is also increased leading to deterioration of sensitivity properties of recording media. For this reason, the present inventors focused on the long-chain aliphatic hydrocarbon group which is considered to be another element dominating the structure and moreover, various investigations were conducted for the types of hydrogen bond association which largely contribute to coloring and erasing abilities. As a result, it was found that by using urea group as hydrogen bond association, it is possible to obtain high color optical density and erasing ability. And further, the length balance of aliphatic hydrocarbon was focused for investigation.

As a result, it was found that by making carbon number of alkyl group as long-chain aliphatic hydrocarbon group longer in chain length, stability in a coloring condition is remarkably improved. When the carbon number of alkyl group is 22 or less, stability in a coloring condition is inappropriate and there is a crucial problem in preservability of image parts relative to the image preservability at 60° C. required for the industry employed as distribution tags or process instructions which requires higher image preservability compared to that of office industry. However, by having a carbon number of 23 or more, coloring condition at 60° C. is remarkably improved and it becomes possible to obtain high image retention rate.

This is because, even though the temperature at which erasing starts from the coloring condition depends on the chain length of alkyl group and it is 60° C. or less when carbon number is 22, the temperature at which erasing starts becomes 60° C. or more with the carbon number of 23 or more and a dramatic change emerges relative to the image preservability at 60° C.

Furthermore, it became apparent that even if the alkyl chain length is made longer, the melting point of the compound is approximately constant and it does not lead to higher melting point which causes the deterioration of coloring sensitivity.

Moreover, these color developer compounds having alkyl group of carbon number 23 or more exhibit satisfactory erasing with a brief heating at an erasing temperature and excel in high-speed erasing ability even though the coloring condition is stable.

These results became apparent for the first time by the present invention and the production of reversible thermosensitive recording medium having high sensitivity and heat-resistant preservability which excels in high-speed erasing ability and is highly practical for use became possible by these discoveries.

In other words, by introducing urea groups in the molecular structure of color developers and having a platform of alkyl group having carbon number 23 or more according to the present invention, it becomes possible to have appropriate coloring stability without increasing the melting point of color developers and to pursue high coloring sensitivity, storage stability and high-speed erasing ability of image parts simultaneously.

The phenol compound utilized as a color developer of the present invention is expressed by Structural Formula (1) below.

Structural Formula (1)

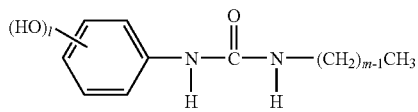

In above Structural Formula (1), "l" represents an integer of 1 to 3, "m" represents an integer of 23 or more and compounds are exemplified by following Structural Formulae (2) to (8) of the present invention.

Structural Formula (2)

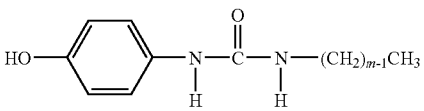

Structural Formula (3)

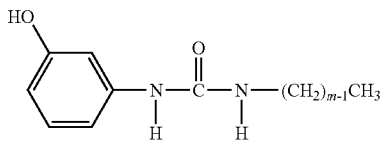

Structural Formula (4)

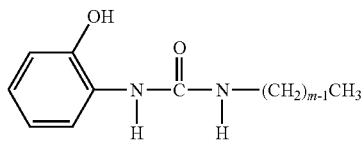

Structural Formula (5)

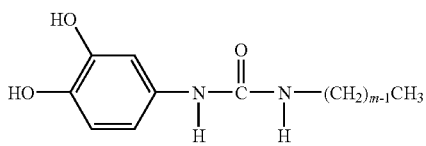

Structural Formula (6)

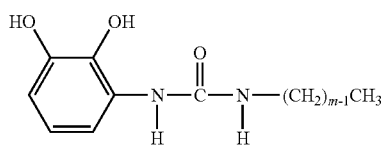

Structural Formula (7)

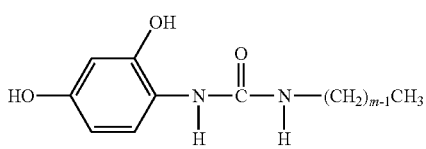

Structural Formula (8)

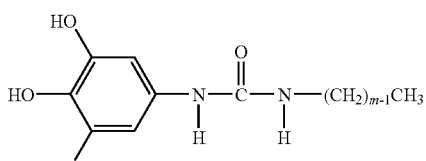

Among the above-mentioned Structural Formulae (2) to (8), the above-mentioned compound of Structural Formula (2) is preferably used as those allowing excellent color developing and/or erasing property.

Of these compounds expressed by the above General Formula (2), compounds in which "m" represents an integer of 23 to 29 are new phenol compounds.

As "m" gets longer, color optical density, erasing optical density and stability of coloring images are improved therefore more appropriate recording medium can be obtained with longer chains. On the other hand, longer chain requires expensive raw materials which may be difficult to obtain and impractical for use. Therefore, the chain length is preferably 23 to 40, more preferably 23 to 35 and most preferably 27 to 35 for obtaining appropriate recording medium properties such as color optical density, erasing optical density, stability of images and high-speed erasing ability and making it practically usable.

The phenol compounds used for the present invention will be exemplified below.

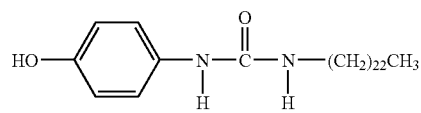

-continued

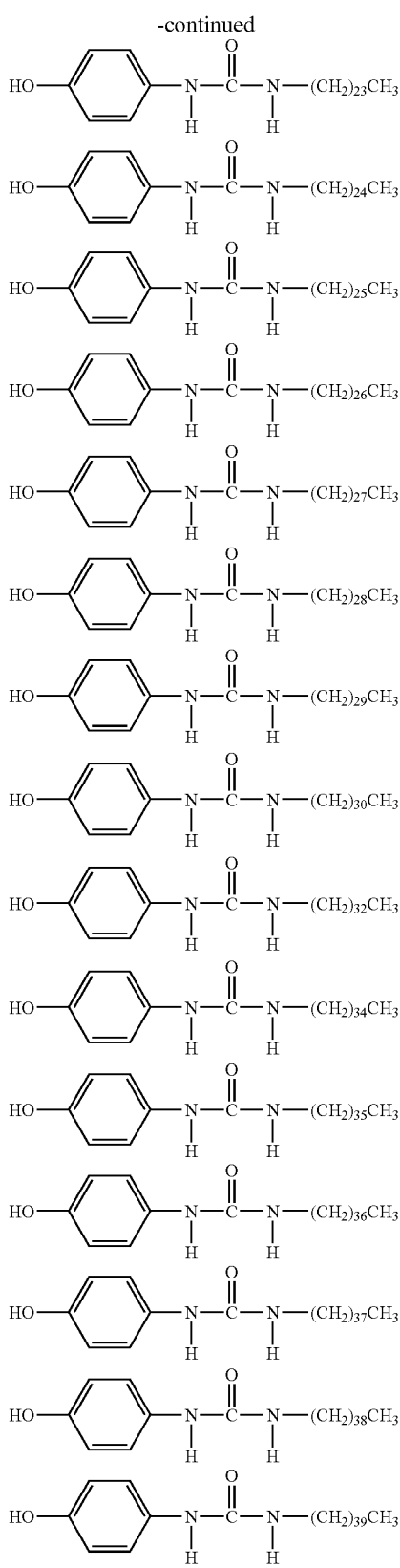

Such phenol compounds are obtained from a coupling reaction with p-aminophenol through a long-chain aliphatic amine-induced long-chain aliphatic isocyanate or a coupling reaction with p-aminophenol through acid chloride from long-chain aliphatic acid or fatty acid ester, azidization and isocyanate. Upon completing condensation reaction with p-aminophenol, the obtained material is normally cooled to a room temperature or further cooled to below the room temperature; added with an acid such as hydrophilic organic solvent liquid of hydrochloric acid, for example; deposits are separated by filteration; washed, dried and then recrystallized using appropriate solvents. If there are both hydroxyl and amino groups, the urethane bond formation reaction and coupling reaction become competitive, on the other hand, in the case of p-aminophenol, condensation reaction progresses dominantly because electron donating ability of hydroxyl group reduces by resonance structure of benzene rings enabling to obtain the phenol compounds highly selectively. The phenol compounds used in the present invention is not limited to this synthesis method.

Further, the leuco dyes for use in the present invention can be used singly or by mixture and are known precursor dyes such as, for example, phthalide compounds, azaphthalide compounds, and fluoran compounds.

Specific examples of the leuco dyes include the following compounds:
2-anilino-3-methyl-6-diethylaminofluoran,
2-anilino-3-methyl-6-di(n-butylamino)fluoran,
2-anilino-3-methyl-6-(N-n-propyl-N-methylamino)fluoran,
2-anilino-3-methyl-6-(N-isopropyl-N-methylamino)fluoran,
2-anilino-3-methyl-6-(N-isobutyl-N-methylamino)fluoran,
2-anilino-3-methyl-6-(N-n-amyl-N-methylamino) fluoran,
2-anilino-3-methyl-6-(N-sec-butyl-N-methylamino)fluoran,
2-anilino-3-methyl-6-(N-n-amyl-N-ethylamino)fluoran
2-anilino-3-methyl-6-(N-iso-amyl-N-ethylamino)fluoran,
2-anilino-3-methyl-6-(N-n-propyl-N-isopropylamino)-fluoran,
2-anilino-3-methyl-6-(N-cyclohexyl-N-methylamino)-fluoran,
2-anilino-3-methyl-6-(N-ethyl-p-toluidino)fluoran,
2-anilino-3-methyl-6-(N-methyl-p-toluidino)fluoran,
2-(3-toluidino)-3-methyl-6-diethylaminofluoran,
2-(m-trichloromethylanilino)-3-methyl-6-diethylaminofluoran,
2-(m-trifluoromethylanilino)-3-methyl-6-diethylaminofluoran,
2-(m-trichloromethylanilino)-3-methyl-6-(N-cyclohexyl-N-methylamino) fluoran,
2-(2,4-dimethylanilino)-3-methyl-6-diethylaminofluoran,
2-(N-ethyl-p-toluidino)-3-methyl-6-(N-ethylanilino)fluoran,
2-(N-ethyl-p-toluidino)-3-methyl-6-(N-propyl-p-toluidino) fluoran,
2-anilino-6-(N-n-hexyl-N-ethylamino)fluoran,
2-(o-chloroanilino)-6-diethylaminofluoran,
2-(o-chloroanilino)-6-dibutylaminofluoran,
2-(m-trifluoromethylanilino)-6-diethylaminofluoran,
2,3-dimethyl-6-dimethylaminofluoran,
3-methyl-6-(N-ethyl-p-toluidino)fluoran,
2-chloro-6-diethylaminofluoran,
2-bromo-6-diethylaminofluoran,
2-chloro-6-dipropylaminofluoran,
3-chloro-6-cyclohexylaminofluoran,
3-bromo-6-cyclohexylaminofluoran,
2-chloro-6-(N-ethyl-N-isoamylamino)fluoran,
2-chloro-3-methyl-6-diethylaminofluoran,
2-anilino-3-chloro-6-diethylaminofluoran,
2-(o-chloroanilino)-3-chloro-6-cyclohexylaminofluoran,
2-(m-trifluoromethylanilino)-3-chloro-6-diethylaminofluoran, 2-(2,3-dichloroanilino)-3-chloro-6-diethylaminofluoran,
1,2-benzo-6-diethylaminofluoran,
3-diethylamino-6-(m-trifluoromethylanilino)fluoran,
3-(1-ethyl-2-methylindole-3-yl)-3-(2-ethoxy-4-diethylaminophenyl)-4-azaphthalide,
3-(1-ethyl-2-methylindole-3-yl)-3-(2-ethoxy-4-diethylaminophenyl)-7-azaphthalide,
3-(1-octyl-2-methylindole-3-yl)-3-(2-ethoxy-4-diethylaminophenyl)-4-azaphthalide,
3-(1-ethyl-2-methylindole-3-yl)-3-(2-methyl-4-diethylaminophenyl)-4-azaphthalide,
3-(1-ethyl-2-methylindole-3-yl)-3-(2-methyl-4-diethylaminophenyl)-7-azaphthalide,
3-(1-ethyl-2-methylindole-3-yl)-3-(4-diethylaminophenyl)-4-azaphthalide,
3-(1-ethyl-2-methylindole-3-yl)-3-(4-N-n-amyl-N-methylaminophenyl)-4-azaphthalide,
3-(1-methyl-2-methylindole-3-yl)-3-(2-hexyloxy-4-diethylaminophenyl)-4-azaphthalide,
3,3-bis(2-ethoxy-4-diethylaminophenyl)-4-azaphthalide, and
3,3-bis(2-ethoxy-4-diethylaminophenyl)-7-azaphthalide.

Appropriate range of the blending ratio of the leuco dye and the color developer varies depending on the combinations of the utilized compounds. The mol ratio of the color developer to the coloring agent is approximately in the range of 0.1 to 20, preferably 0.2 to 10. The color developer amount of over or under this range may result in a lower color optical density. Further, the leuco dye and color developer may be utilized in an encapsulated condition.

Examples of binder resin, which is utilized for forming a thermosensitive recording layer together with the leuco dye and the color developer include polyvinyl chloride, polyvinyl acetate, vinylchloride-vinylacetate copolymers, ethylcellulose, polystyrenes, styrene copolymers, phenoxy resins, polyesters, aromatic polyesters, polyurethanes, polycarbonates, polyester acrylates, polyester methacrylate, acrylic acid copolymers, maleic acid copolymers, polyvinylalcohols, modified polyvinylalcohols, hydroxylethylcellulose, carboxymethylcellulose, and starch. These binder resins serve to prevent the deviation of the respective materials in the composition due to heating for the recording erasures thereby to maintain the uniformly dispersed condition. Accordingly, the binder resin is preferred to be highly heat-resistant. The binder resin may be crosslinked by means of heating, ultraviolet irradiation, electron beam and the like.

Specific examples of the crosslinked resin used for the present invention include such resins, having a group reactive with a cross-linking agent, as acrylpolyol resins, polyesterpolyol resins, polyurethanepolyol resins, phenoxy resins, polyvinylbutyral resins, celluloseacetate propionate resins, and celluloseacetate butyrate resins, and copolymer resins between a monomer having a group reactive with a crosslinking agent and another monomer, but in the present invention, the crosslinked resin is not limited to these compounds.

Further, the crosslinked resin having a hydroxyl value of 70 KO Hmg/g or more is preferably contained (initially used) in the present invention. Examples of the resin having a hydroxyl value of 70 KO Hmg/g or more include acrylpolyol resins, polyesterpolyol resins, polyurethanepolyol resins, or the like are employed, but, in particular, the acrylpolyol resins are preferably employed for satisfactory stability of coloring and satisfactory erasability. The hydroxyl value is 70 KO Hmg/g or more and particularly preferably 90 KO Hmg/g or more. The level of the hydroxyl value is related to the crosslinking density; therefore it affects the chemical resistance, properties and the like of the coating. The present inventors have found that the resins having a hydroxyl value of 70 KO Hmg/g or more enhances the durability, surface hardness of the coating, and cracking resistance. Whether or not the reversible thermosensitive recording material utilizes the resin having a hydroxyl value of 70 KO Hmg/g or more can be confirmed, for example, by analyzing the amount of remaining hydroxyl groups and the amount of ether bond.

The acrylpolyol resins have different properties depending on their composition, as a monomer having hydroxyl group, hydroxyethylacrylate (HEA), hydroxypropylacrylate (HPA), 2-hydroxyethylmethacrylate (HEMA), 2-hydroxypropylmethacrylate (HPMA), 2-hydroxybutylmonoacrylate (2-HBA), 1,4-hydroxybutylmonoacrylate (1-HBA), or the like is used. Among them, the monomer having a primary hydroxyl group such as 2-hydroxyethylmethacrylate is suitably utilized, in light of superior cracking resistance and durability of the coating.

As a curing agent used for the present invention, examples include conventional isocyanate compounds, amine compounds, phenol compounds, epoxy compounds and the like. Among these compounds, isocyanate-based curing agent is suitably utilized. The isocyanate compound used here may be selected from various derivatives of known isocyanate monomer such as urethane-modified, allophanate-modified, isocyanurate-modified, buret-modified, and carbodiimide-modified compounds, and blockedisocyanate compounds. Examples of the isocyanate monomer, which may yield the modified compounds, include tolylenediisocyanate (TDI), 4,4'-diphenylmethanediisocyanate (MDI), xylylenediisocyanate (XDI), naphthylenediisocyanate (NDI), paraphenylenediisocyanate (PPDI), tetramethylxylylenediisocyanate (TMXDI), hexamethylene diisocyanate (HDI), dicyclohexylmethanediisocyanate (HMDI), isophoronediisocyanate (IPDI), lysinediisocyanate (LDI), isopropylidenebis(4-cyclohexylisocyanate) (IPC), cyclohexyldiisocyanate (CHDI), and tolidinediisocyanate (TODI), but in the invention, the curing agent is not limited to these compounds.

Further, as the crosslinking promoter, a catalyst may be employed which is utilized in general for such reaction. Examples of the crosslinking promoter include tertiary amines such as 1,4-diaza-bicyclo[2,2,2]octane, and metal compounds such as organic tin compounds. Further, all of the introduced curing agent may not necessarily react for the crosslinking. That is, the curing agent may be remained in unreacted condition. Such crosslinking reaction may progress with time; therefore, the presence of unreacted curing agent does not indicate that the crosslinking reaction has not progressed at all, nor suggests that the crosslinked resins do not exist, even if the unreacted curing agent is detected. Further, an immersion test of polymer into a solvent with a high solubility may be employed for distinguishing whether or not the polymer is in crosslinked condition. That is, the non-crosslinked polymer cannot remain in the solute since such polymer dissolves into the solvent, an analysis may be properly carried out for examining the existence of the polymer in the solute.

Further, according to the present invention, the recording layer may contain, together with the above-mentioned color developer and the leuco dye, a color developing and erasing controlling agent having straight-chain hydrocarbon group and hydrogen-containing groups such as an amide group and a urea group. Thus, satisfactory preservation stability of color images can be achieved, at the same time, erasability during erasing is also improved and satisfactory erasing property can be achieved.

Moreover, according to the present invention, a protective layer which contains the crosslinked resin may be provided on the reversible thermosensitive recording layer. The resin for use in the protective layer include, as in the above-mentioned recording layer, thermosetting resins, UV curable resins, electron beam curable resins.

Particularly preferably, the resins for use in the protective layer are ultraviolet-absorbing polymers having an ultraviolet-absorbing group in the molecular structure thereof.

As the ultraviolet-absorbing polymer, polymers composed of a monomer having an ultraviolet-absorbing group and a monomer having a functional group capable of being crosslinked are preferably used. As the monomer having an ultraviolet-absorbing group, monomers having benzotriazole skeleton such as (2'-Hydroxy-5'-methacryloxyethylphenyl)-2H-benzotriazole, 2-(2'-Hydroxy-5'-methylphenyl)benzotriazole, and 2-(2'-Hydroxy-3'-ω-butyl-5'-methylphenyl)-5-chlorobenzotriazole are particularly preferably used.

Further, examples of the monomer containing a functional group include 2-isopropenyl-2-oxazoline, 2-aziridinylethyl (meth)acrylate, methacrylic acid, glycidyl (meth)acrylate, hydroxyethyl (meth)acrylate, hydroxylpropyl (meth)acrylate, dimethylaminoethyl (meth)acrylate, diethylaminoethyl (meth)acrylate, t-butylaminoethyl (meth)acrylate, tetrahydrofurfuryl (meth)acrylate, and among them, hydroxyethyl (meth)acrylate, hydroxylpropyl (meth)acrylate, and the like are particularly preferably used.

Further, in order to enhance coating strength and heat resistance, the following monomer may be copolymerized with copolymers of the monomer containing an ultraviolet-absorbing group and the monomer containing a functional group. Examples thereof include monomers such as styrene, styrene-butadiene, styrene-isobutylene, ethylenevinyl acetate, vinyl acetate, methacrylonitrile, vinyl alcohol, vinyl pyrrolidone, acrylonitrile, and methacrylonitrile; (meth) acrylic esters which do not contain the functional group such as acrylic acid, methyl (meth)acrylate, ethyl (meth)acrylate, propyl (meth)acrylate, butyl (meth)acrylate, isobutyl (meth) acrylate, t-butyl (meth)acrylate, ethylhexyl (meth)acrylate, octyl (meth)acrylate, isodecyl (meth)acrylate, lauryl (meth) acrylate, lauryl tridecyl (meth)acrylate, tridecyl (meth)acrylate, cetylstearyl (meth)acrylate, stearyl (meth)acrylate, cyclohexyl (meth)acrylate, and benzyl (meth)acrylate; monomers which have two or more polymerizable double bond in one molecule thereof such as ethylene di(meth)acrylate, diethylene glycol di(meth)acrylate, triethylene glycol di(meth)acrylate, tetraethylene glycol di(meth)acrylate, decaethylene glycol di(meth)acrylate, pentacontahecta ethylene glycol (meth)acrylate, butylene di(meth)acrylate, pentaerythritol tetra(meth)acrylate, trimethylolpropane tri(meth) acrylate, pentadeca ethylene glycol di(meth)acrylate, and diethylene glycol phthalate di(meth)acrylate, but not limited to these examples. Among them, styrene, methyl (meth)acrylate, ethyl (meth)acrylate, propyl (meth)acrylate, butyl (meth)acrylate, isobutyl (meth)acrylate, t-butyl (meth)acrylate and the like are particularly suitably used. Further, combination of two or more may be used accordingly.

From the above description, specific suitable examples of the polymer having ultraviolet-absorbing structure, which is used in the present invention, include copolymers composed of 2-(2'-hydroxy-5'-methacryloxyethyl phenyl)-2H-benzotriazole, 2-hydroxyethyl methacrylate and styrene; copolymers composed of 2-(2'-hydroxy-5'-methylphenyl) benzotriazole, 2-hydroxypropyl methacrylate and methyl methacrylate; and the like, but the polymer having ultraviolet-absorbing structure is not particularly limited to these examples. The content of ultraviolet-absorbing polymer contained in the protective layers is preferably 20% by mass to 80% by mass.

Further, according to the present invention, the protective layer may contain ultraviolet-absorbing inorganic fine particles.

The inorganic pigment is not particularly limited provided that the pigment has an average particle diameter of 0.1 μm or less. Examples of such inorganic pigment include such metal oxides and metal complex oxides as zinc oxide, indium oxide, alumina, silica, zirconium oxide, tin oxide, cerium oxide, iron oxide, antimony oxide, barium oxide, calcium oxide, bismuth oxide, nickel oxide, magnesium oxide, chromium oxide, manganese oxide, tantalum oxide, niobium oxide, thorium oxide, hafnium oxide, molybdenum oxide, iron ferrite, nickel ferrite, cobalt ferrite, barium titanate and potassium titanate, such metal sulfides or sulfates as zinc sulfide and barium sulfate, such metal carbides as titanium carbide, silicon carbide, molybdenum carbide, tungsten carbide and tantalum carbide, and such metal nitride as aluminum nitride, silicone nitride, boron nitride, zirconium nitride, vanadium nitride, titanium nitride, niobium nitride, and gallium nitride.

Among them, pigments having absorption end in the wavelength region of 400 nm or less are particularly preferred.

These pigments are classified into two groups: (A) pigments having absorption end in the UV-A region of the spectrum, i.e., wavelength of 320 nm to 400 nm, (B) inorganic pigments having absorption end in the shorter wavelength region than the UV-A region. In the present invention, the inorganic pigment (A) or inorganic pigment (B) can be used alone, but use of the inorganic pigment (A) and inorganic pigment (B) in combination makes the effect of the present invention more remarkable. When the inorganic pigment (A) or inorganic pigment (B) is used alone, these pigments may be contained in an intermediate layer or the protective layer. Further, when the inorganic pigment (A) and inorganic pigment (B) is used in combination, these pigments may be contained in the intermediate layer or the protective layer at the same time, but the inorganic pigment (A) and inorganic pigment (B) may be separately contained in the intermediate layer or the protective layer. In this case, the inorganic pigment (A) may be contained in the intermediate layer and the inorganic pigment (B) may be contained in the protective layer, by which the effect of the present invention can be achieved more remarkably.

Specific examples of the above-noted inorganic pigment (A) include zinc sulfide, titanium oxide, indium oxide, cerium oxide, tin oxide, molybdenum oxide, zinc oxide, and gallium nitride.

Further, specific examples of the inorganic pigment (B) include silica, alumina, silica-alumina, antimony oxide, magnesium oxide, zirconium oxide, barium oxide, calcium oxide, strontium oxide, silicone nitride, aluminum nitride, boron nitride, and barium sulfate. The content of ultraviolet-absorbing inorganic fine particles contained in the protective layers is preferably 5% by mass to 80% by mass.

Further, in the present invention, inorganic or organic filler, lubricant, etc. which are used in this kind of recording medium may be used in the protective layer.

The support of the reversible thermosensitive recording medium of the present invention may be, for example, paper, resin film, PET film, synthetic paper, metal foil, glass, or complexes thereof, and may be those capable of retaining the thermosensitive recording layer. Further, those having the thickness according to necessity can be used alone or by, for example, bonding. Specifically, supports having any thickness from about a few micrometers to about a few millimeters, preferably 60 μm to 150 μm, may be used.

Further, when an under layer is provided on these supports, disposing the under layer via an adhesion layer prevents occurrence of cracks and decreases occurrence of burrs.

The adhesion layer can be formed, for example, by the similar coating method as that employed in the above-mentioned respective layers.

The reversible thermosensitive recording medium may be formed into various shapes depending on the application such as card-like, sheet-like, label-like, or roll-like shapes.

The applications of the recording medium formed into a card-like shape include prepaid card, point card and also credit card. The recording medium formed into a sheet-like shape of normal document size such as A4 size may be applied broadly into temporary output applications such as normal document, instructing letter for process management, circulation document, and conference data, needless to say trial printings, owing to the wider printable area than the card-like size when an printing-erasing apparatus is introduced.

The recording medium formed into a roll-like shape may be applied for display board, notice plate and electronic white board by being integrated into an instrument with a printing-erasing part. Such display instruments may be appropriately utilized in a clean room since dusts and contaminants are not emitted.

It is possible to obtain a rewritable record having appropriate coloring sensitivity, color optical density and image preservability and is practically usable by utilizing the reversible thermosensitive recording medium of the present invention.

(Reversible Thermosensitive Recording Member)

According to the reversible thermosensitive recording member of the present invention, the reversibly displayable thermosensitive layer and the information-memorizing part are provided in one card (integrated), and a part of the memorized information of the information-memorizing part is displayed on the thermosensitive layer, thereby making it convenient for the card owner to receive information which can be achieved only by viewing the card without use of any particular device. Further, in the case that the content of the information-memorizing part is overwritten; the reversible thermosensitive recording medium may be repeatably utilized by overwriting the display of the reversible thermosensitive recording part.

The member having the information-memorizing part and the reversible displaying part may be classified into the following two types.

(1) A part of the member where the information-memorizing part is utilized as a support of the reversible thermosensitive recording medium, and the thermosensitive layer is disposed on the support directly.

(2) A thermosensitive layer is disposed separately on a support to form a reversible thermosensitive recording medium, and the support is adhered to the member having the information-memorizing part.

In the cases of (1) and (2), the position of the disposed information-memorizing part may be the opposite side of the thermosensitive layer on the support of the reversible thermosensitive recording medium, between the support and the thermosensitive layer, or on a part of the thermosensitive layer, provided that the information-memorizing part and the reversible displaying part are designed to perform their functions.

The information-memorizing part is not particularly limited. For example, it may be preferably formed of a magnetic thermosensitive layer, magnetic stripe, IC memory, optical memory, RF-ID tag card, hologram, and the like. In the sheet medium of which the size is larger than the card size, the IC memory and RF-ID tag are preferably employed. By the way, the RF-ID tag is composed of an IC chip and an antenna connected to the IC chip.

The magnetic thermosensitive layer may be formed by applying a coating material containing conventional iron oxide, barium ferrite etc. and vinylchloride resins, urethane resins, nylon resins etc., on a support or by vapor deposition, spattering etc. without use of resins. The magnetic thermosensitive layer may be provided on the face of the support opposite to the thermosensitive layer, between the support and the thermosensitive layer, or on a part of the thermosensitive layer. Further, the reversible thermosensitive material for displaying may be employed for the memorizing part in a form of barcode, two dimensional codes and the like. Among them, magnetic recording and IC are more preferable.

As for the hologram, the rewritable type is preferred, for example, the rewritable hologram in which coherent light is written on a liquid crystal film of azobenzene polymer is exemplified.

The member having the information recording part typically includes a card, disc, disc cartridge, and tape cassette. Specifically, examples of the member include a thick card such as IC card and optical card; disc cartridge containing an information-rewritable disc such as flexible disc, optical magnetic disc (MD) and DVD-RAM; disc in which disc cartridge is not utilized, e.g. CD-RW; overwrite type disc such as CD-R; optical information recording medium with phase-changing recording material (CD-RW); and video cassette.

Further, the member having both parts of information-memorizing and reversible displaying contributes to the betterment of convenience. For example, a card owner can receive information only by viewing the card without a use of particular device through a display of the part of the information memorized in the information recording part on the thermosensitive layer, more convenient than the card not corresponding to the reversible thermosensitive recording medium.

The information-memorizing part may be properly selected depending on the application without particular limitations provided that the necessary information may be recorded. Examples include a magnetic recording, contact type IC, non-contact type IC and optical memory.

The magnetic thermosensitive layer may be formed by applying a coating material containing metallic compounds such as conventional iron oxide, barium ferrite etc. and vinylchloride resins, urethane resins, nylon resins etc. on a support, otherwise by vapor deposition, spattering etc. using the metallic compounds without use of resins. Further, the thermosensitive layer of the reversible thermosensitive recording medium for displaying may be employed for the memorizing part in a form of barcode, two dimensional codes and the like.

More specifically, the reversible thermosensitive recording medium of the present invention may be appropriately employed for the reversible thermosensitive recording label, reversible thermosensitive recording member, image-processing apparatus and image-processing method. In the present invention, "surface of the reversible thermosensitive recording medium" indicates a surface of the thermosensitive layer side which is not limited to the protective layer, but also include all of or part of the surface which comes in contact with the thermal head during printing and erasing such as the surface of the printing layer or OP layer.

(Reversible Thermosensitive Recording Label)

The reversible thermosensitive recording label contains one of an adhesive layer and tacky layer on an exposed surface of the reversible thermosensitive recording medium opposite to the exposed surface on which an image is formed (in the case that the thermosensitive layer exists on the support, an exposed surface of the support opposite to the surface on which the thermosensitive layer is formed), and other layers properly selected depending on the necessity. Further, in the case that the support of the reversible thermosensitive recording medium is of heat fusion, the adhesive layer or tacky layer on a surface of the support opposite to the surface on which the thermosensitive layer is formed may be omitted.

The shape, configuration, size and the like of the adhesive layer or tacky layer may be properly selected depending on the application without particular limitations. The shape may be sheet-like or film-like; the configuration may be of single layer or laminated layers; and the size may be larger or smaller than the thermosensitive layer.

The material of the adhesive layer or tacky layer may be properly selected depending on the application without particular limitations. Examples of the material include urea resins, melamine resins, phenolic resins, epoxy resins, polyvinyl acetate resins, vinyl acetate-acrylic copolymers, ethylene-vinyl acetate copolymers, acrylic resins, polyvinyl ether resins, vinyl chloride-vinyl acetate copolymers, polystyrene resins, polyester resins, polyurethane resins, polyamide resins, chlorinated polyolefin resins, polyvinyl butyral resins, acrylic ester copolymers, methacrylic ester copolymers, natural rubber, cyanoacrylate resins, silicone resins. These may be used alone or in combination. Further the material may be of hot-melt type, and may be used either with a disposable release paper or without a disposable release paper.

The reversible thermosensitive recording label is normally utilized in a configuration laminated to a substrate sheet such as a card, in which the reversible thermosensitive recording label may be laminated on the entire or part of the substrate sheet, or on one side or both sides.

The shape, configuration, size and the like of the substrate sheet may be properly selected depending on the application without particular limitations. The shape may be plate-like or the like; the configuration may be of single layer or laminated layers; and the size may be properly selected depending on the size of the reversible thermosensitive recording medium. For example, the substrate may be a sheet or laminated body formed of chlorine-containing polymers, polyester resins, biodegradable plastic resins and the like.

The chlorine-containing polymer may be properly selected depending on the application without particular limitations. Examples of the polymer include polyvinyl chloride, vinyl chloride-vinyl acetate copolymers, vinylchloride-vinylacetate-vinylalcohol copolymers, vinylchloride-vinylacetate-maleicacid copolymers, vinylchloride-acrylate copolymers, polyvinylidenechloride, vinylidenechloride-vinylchloride copolymers, and vinylidenechloride-acrylonitrile copolymers.

Examples of the polyester resins include polyethylene terephthalate (PET), polybutylene terephthalate (PBT), alternatively condensed esters of acid ingredients such as terephthalic acid, isophthalic acid, and alcohol ingredients such as ethylene glycol, cyclohexanedimethanol (e.g. PETG, trade name by Eastman Chemical Co.).

Examples of the biodegradable plastic resins include natural polymer resins containing polylactic acid, starch, denaturized polyvinyl alcohol and the like, and microbiological product resins including beta-hydroxybutyric acid and beta-hydroxyvaleric acid.

Further, the substrate may be synthetic resin sheet or paper formed of polyacetate resins, polystyrene (PS) resins, epoxy resins, polyvinylchloride (PVC) resins, polycarbonate (PC) resins, polyamide resins, acryl resins, silicone resins and the like. These materials may be properly combined or laminated.

As for the laminated body, the body containing a core sheet formed of laminated two sheets of white polyvinyl chloride resin of 250 μm thickness and two laminated over sheet of transparent polyvinyl chloride resin of 100 μm thickness on both surfaces of the core sheet may be exemplified. Also the laminate body containing a core sheet formed of laminated two sheets of white PETG of 250 μm thickness and two laminated over sheet of transparent PETG of 100 μm thickness on both surfaces of the core sheet may be exemplified.

When at least one of adhesive layer and tacky layer exist in the reversible thermosensitive recording label, the reversible thermosensitive recording label may be affixed on an entire or a part of a thick substrate such as polyvinylchloride card with magnetic stripes to which the thermosensitive layer is usually difficult to be affixed, thereby a part of the information memorized in magnetic may be displayed.

The reversible thermosensitive recording label may be an alternative to a thick card such as IC card and optical card, flexible disc, disc cartridge containing rewritable disc such as optical magnetic recording disc (MD) and DVD-RAM, disc without disc cartridge such as CD-RW, write-once disc such as CD-R, optical information recording medium (CD-RW) based on phase-change recording material and display label on video cassette.

Figure 2:
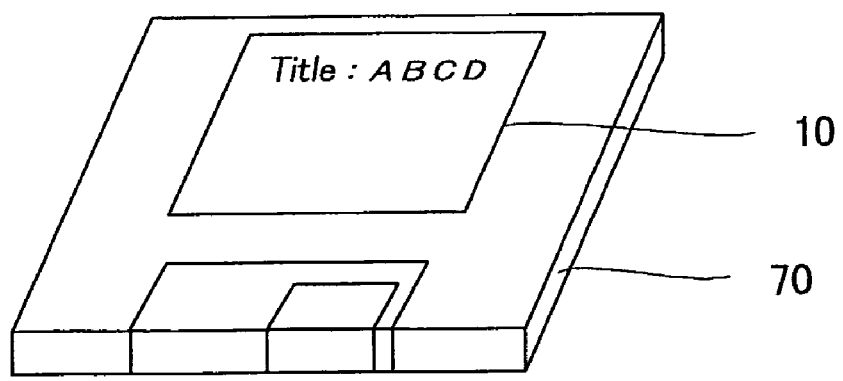
FIG. 2 is a diagram exemplifying a configuration, in which a reversible thermosensitive recording label is laminated on an MD disc cartridge.

FIG. 2 exemplifies the reversible thermosensitive recording label 10 of the present invention affixed to MD disc cartridge 70. In this case, such application is allowable that the displayed content is automatically altered depending on the alternation of the memorized content in the MD. Further, in the case of a disc without disc cartridge such as CD-RW, the reversible thermosensitive recording label of the present invention may be directly affixed to the disc.

Figure 3:
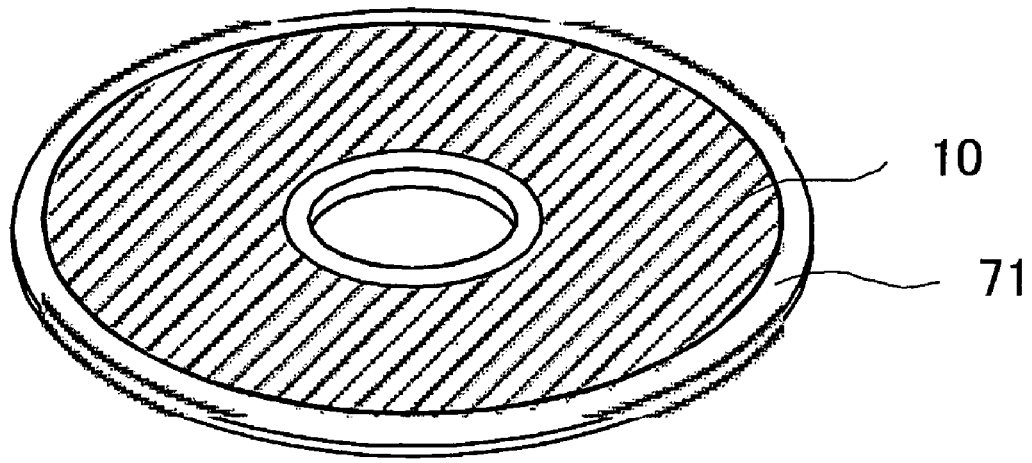
FIG. 3 is a diagram exemplifying a configuration, in which a reversible thermosensitive recording label is laminated on a CD-RW.

FIG. 3 exemplifies the reversible thermosensitive recording label 10 of the present invention affixed to CD-RW 71. In this case, the reversible thermosensitive recording label is affixed on a write-once disc such as CD-R in place of CD-RW, then a part of the memorized information in the CD-R may be rewritten and displayed.

Figure 4:
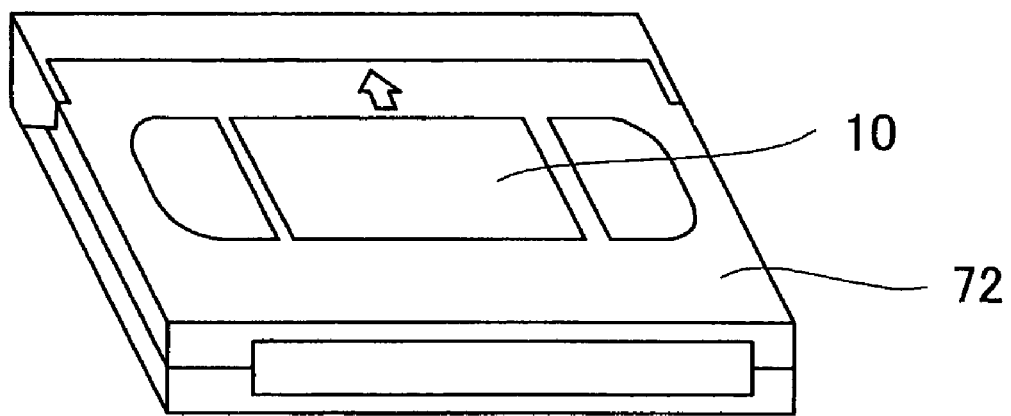
FIG. 4 is a diagram exemplifying a configuration, in which a reversible thermosensitive recording label is employed on a video cassette as a display label.

FIG. 4 shows an example where the reversible thermosensitive recording label 10 of the present invention is affixed to a video cassette 72. In this case, such application is allowable that the display is automatically altered depending on the change of the memories in the video cassette.

(Image-Processing Method and Image-Processing Apparatus)

The image-processing apparatus of the present invention contains at least one of image-forming unit and image-erasing unit and the other unit properly selected depending on the necessity such as conveying unit, control unit and the like.

The image-processing method of the present invention performs at least one of forming images and erasing images by heating the reversible thermosensitive recording medium and contains the other operations properly selected depending on the necessity such as conveying, controlling and the like.

The image-processing method of the present invention may be properly carried out by means of the image-processing apparatus of the present invention. And at least one of the image forming and erasing through heating of the reversible thermosensitive recording medium may be carried out by at least one of the image-forming and image-erasing units and other operations may be carried out by means of other units.

—Image-Forming Unit and Image-Erasing Unit—

The image-forming unit is the unit in which images are formed through heating the reversible thermosensitive recording medium. The image-erasing unit is the unit in which images are erased through heating the reversible thermosensitive recording medium.

The image-forming unit may be properly selected depending on the application from a thermal head, laser irradiation apparatus and the like. These may be used alone or in combination.

The image-erasing unit may be properly selected depending on the application from a hot stamp, ceramic heater, heat roller, heat block, hot blow, thermal head, laser irradiation apparatus and the like. Among them, the ceramic heater is preferred. By means of the ceramic heater, the apparatus may be miniaturized, the erasing condition may be stabilized and images with high contrast may be obtained. The operating temperature of the ceramic heater may be properly selected depending on the application, preferably 110° C. or more, more preferably 112° C. or more, most preferably 115° C. or more, for example.

The apparatus may be more minitualized by means of the thermal head, in addition, the electric power consumption may be saved and the power supply may be replaced by a handy type. Further, the performance of image forming and erasing may be combined into one thermal head, thereby the apparatus may be minitualized further. When recording and erasing are performed with one thermal head, new images are recorded after former images are once erased; alternatively an overwrite type may be provided in which the individual image is erased at variable energy level and new images are recorded. In the overwrite type, the total period for recording and erasing is relatively short, resulting in the speed-up of the recording.

In the case that the reversible thermosensitive recording member (card) with the thermosensitive layer and information memorizing part is utilized, the reading unit and rewriting unit for the memories in the information memorizing part are also included in the apparatus.

The conveying unit may be properly selected depending on the application, provided that the unit performs conveying of the reversible thermosensitive recording media successively; a conveying belt, conveying roller, and combination of conveying belt and conveying roller may be exemplified.

The control unit may be properly selected depending on the application, provided that the unit can control the respective steps such as sequencer, computer, and the like.

Here, one aspect of the image-processing method of the present invention through the image-processing apparatus of the present invention will be explained with reference to FIGS. 5A and 5B. The image-processing apparatus shown in FIG. 5A contains thermal head 53 as a heating unit, ceramic heater 38, magnetic head 34 and conveying rollers 31, 40 and 47.

Figure 5A:
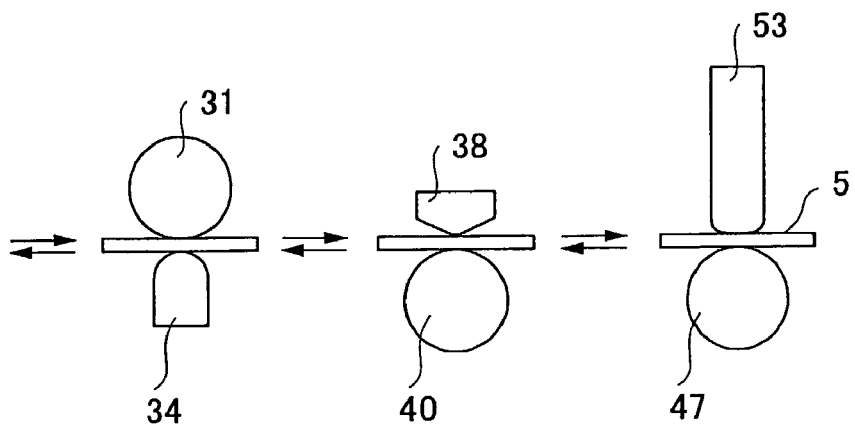
FIG. 5A schematically exemplifies an image-processing apparatus, wherein the image erasing is carried out by a ceramic heater, and the image forming is carried out by a thermal head respectively.

As shown in FIG. 5A, in this image-processing apparatus, the information memorized in the magnetic thermosensitive layer of the reversible thermosensitive recording medium is initially read by the magnetic head. Then, heating by means of the ceramic heater erases the images recorded in the thermosensitive layer. Further, the new information processed based on the information read by the magnetic head is recorded in the reversible thermosensitive layer with the thermal head. Thereafter, the information in the magnetic thermosensitive layer is replaced by new information.

In the image-processing apparatus shown in FIG. 5A, the reversible thermosensitive recording medium 5 in which the magnetic thermosensitive layer is provided on the opposite side of the thermosensitive layer, is conveyed along the conveying root (shown by back-forth arrows) or conveyed in the reverse direction along the conveying root. The reversible thermosensitive recording medium 5 is subjected to magnetic recording or erasing in the magnetic thermosensitive layer between the magnetic head 34 and the conveying roller 31, and subjected to a heat treatment for erasing images between the ceramic heater 38 and the conveying roller 40, and then images are formed between the thermal head 53 and conveying roller 47, thereafter discharged out of the apparatus. As explained earlier, the ceramic heater 38 is preferably set at 110° C. or more, more preferably 112° C. or more and most preferably 115° C. or more. By the way, rewriting of the magnetic recording may be performed before or after the image erasing by means of the ceramic heater. In addition, the recording medium is conveyed reversibly after passing between the ceramic heater 38 and conveying roller 40 or after passing between the thermal head 53 and conveying roller 47, if necessary. The duplicated heat treatment by means of ceramic heater 38 and the duplicated printing by means of thermal head 53 may be applied in some instances.

Figure 5B:
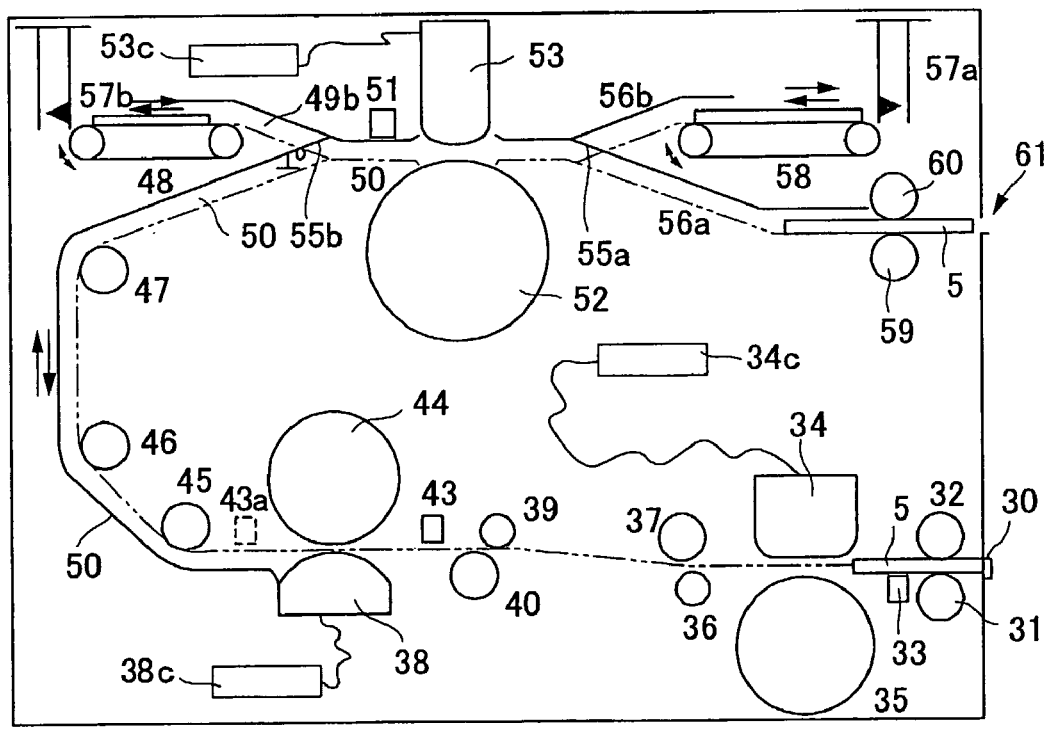
FIG. 5B schematically exemplifies an image-processing apparatus of the present invention.
Figure 6A:
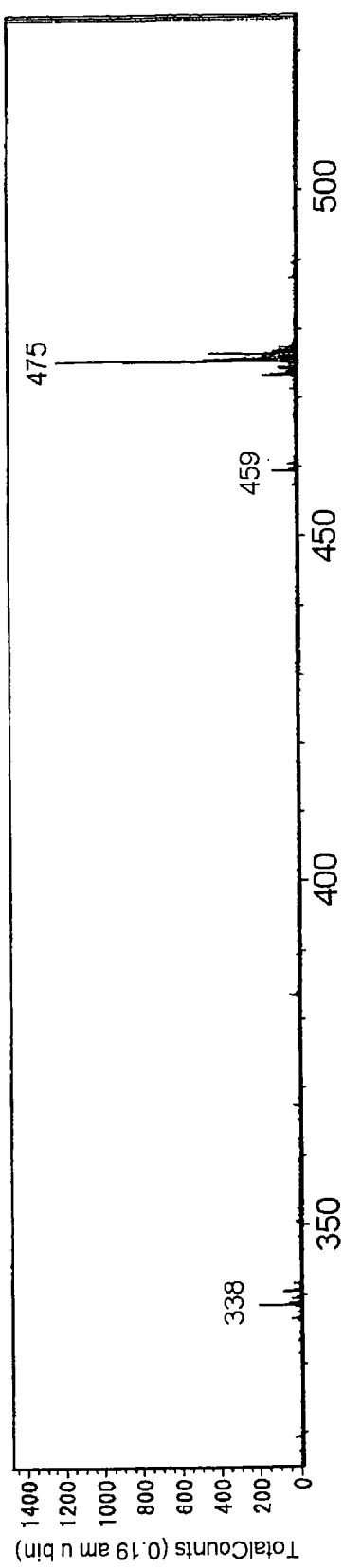
FIG. 6A shows a positive ion peak profile of a synthesized compound in Example 1 used for the present invention obtained by use of a time-of-flight secondary ion mass spectrometer.
Figure 6B:
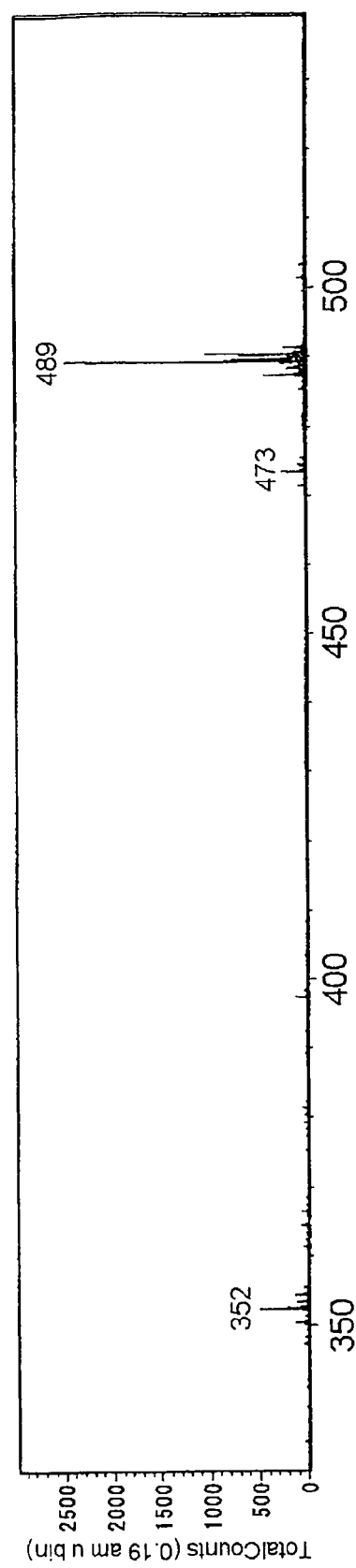
FIG. 6B shows a positive ion peak profile of a synthesized compound in Example 2 used for the present invention obtained by use of a time-of-flight secondary ion mass spectrometer.
Figure 6E:
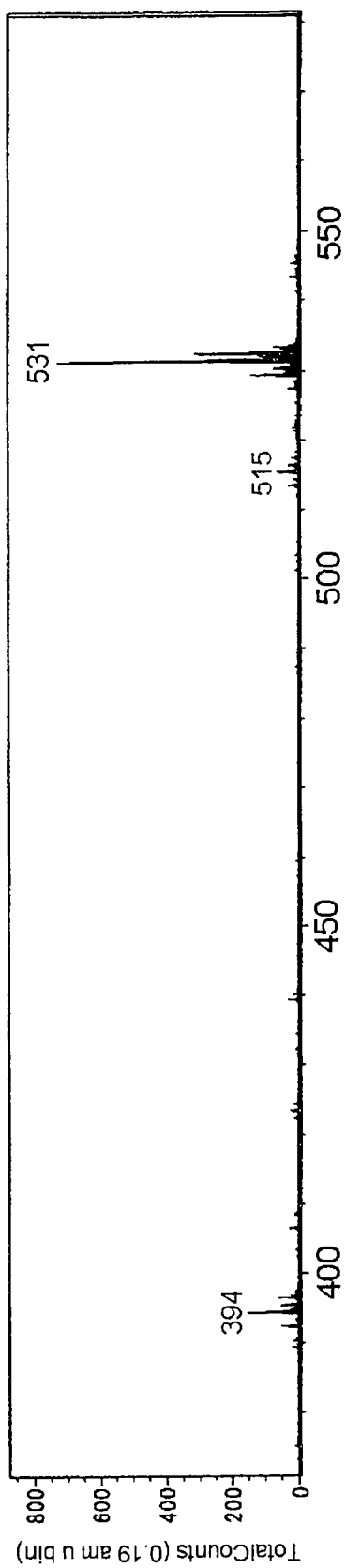
FIG. 6E shows a positive ion peak profile of a synthesized compound in Example 5 used for the present invention obtained by use of a time-of-flight secondary ion mass spectrometer.
Figure 6F:
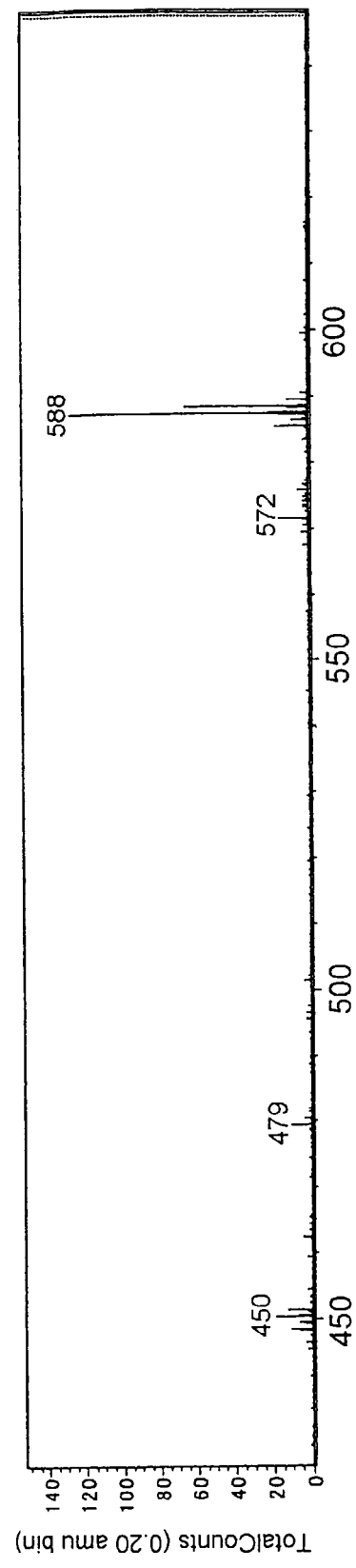
FIG. 6F shows a positive ion peak profile of a synthesized compound in Synthetic Example 1 used for the present invention obtained by use of a time-of-flight secondary ion mass spectrometer.
Figure 6G:
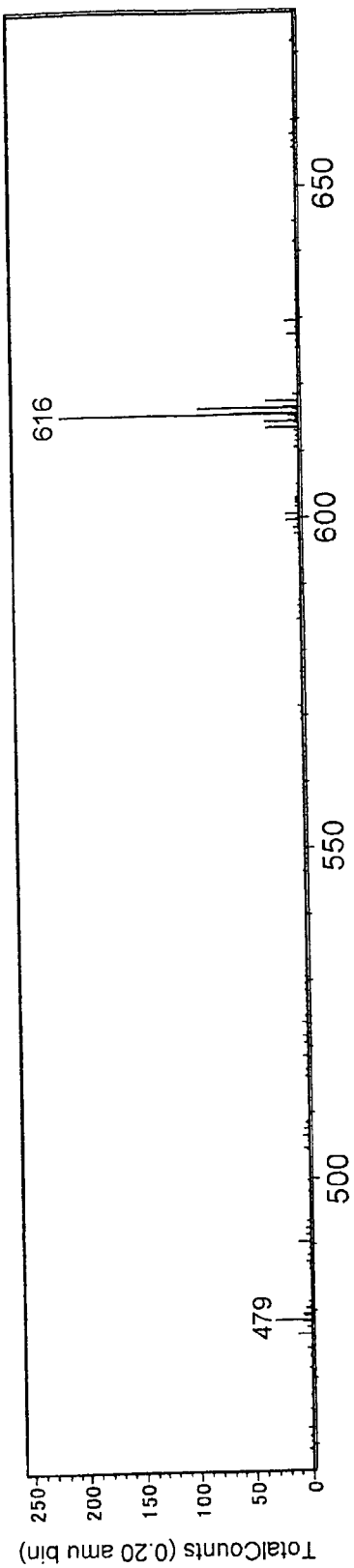
FIG. 6G shows a positive ion peak profile of a synthesized compound in Synthetic Example 2 used for the present invention obtained by use of a time-of-flight secondary ion mass spectrometer.
Figure 6H:
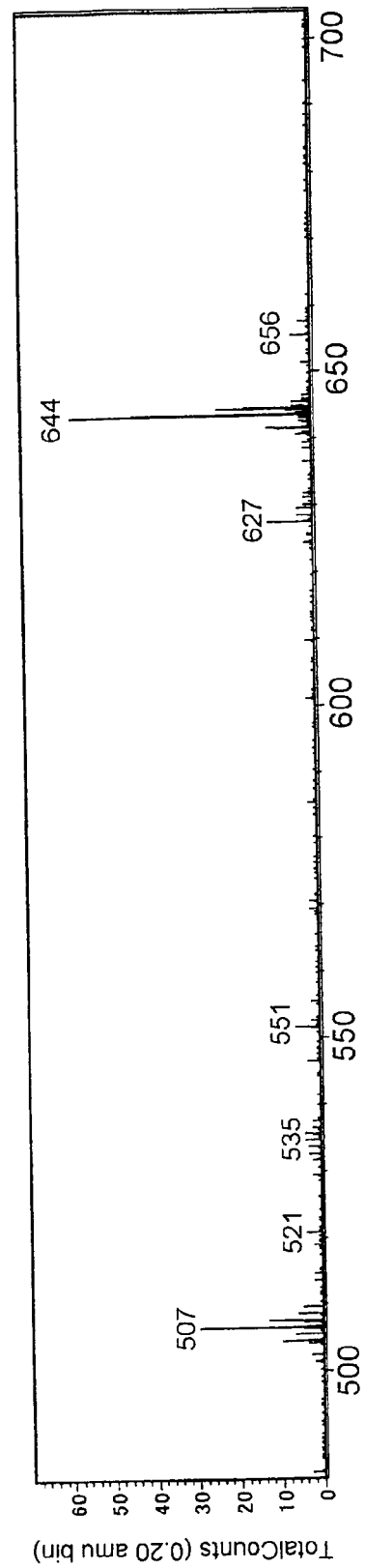
FIG. 6H shows a positive ion peak profile of a synthesized compound in Synthetic Example 3 used for the present invention obtained by use of a time-of-flight secondary ion mass spectrometer.
Figure 7A:
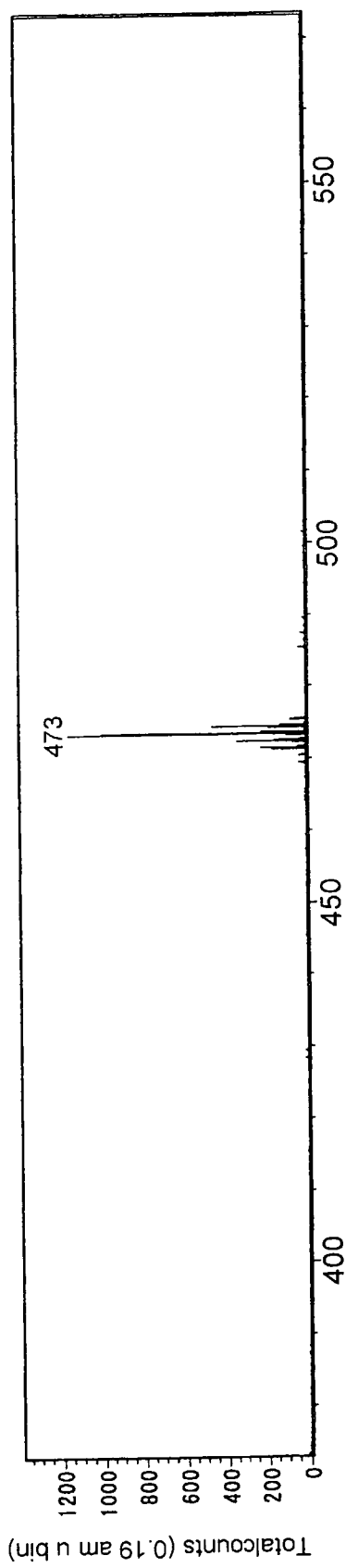
FIG. 7A shows a negative ion peak profile of a synthesized compound in Example 1 used for the present invention obtained by use of a time-of-flight secondary ion mass spectrometer.
Figure 7B:
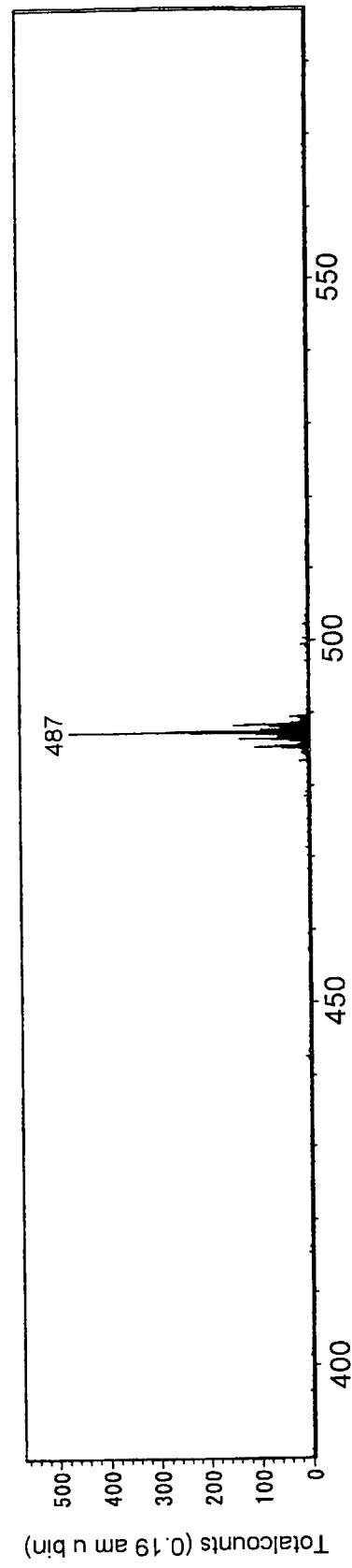
FIG. 7B shows a negative ion peak profile of a synthesized compound in Example 2 used for the present invention obtained by use of a time-of-flight secondary ion mass spectrometer.
Figure 7C:
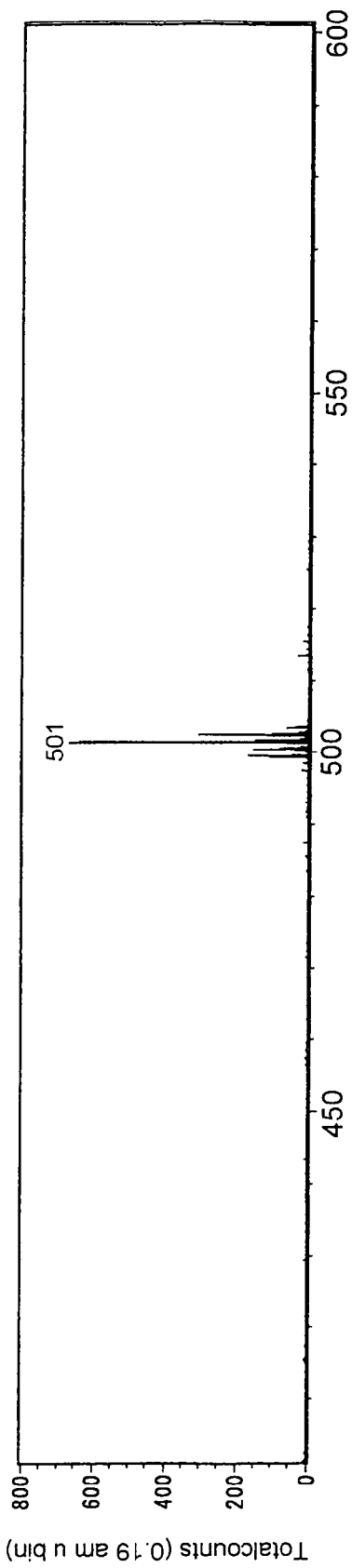
FIG. 7C shows a negative ion peak profile of a synthesized compound in Example 3 used for the present invention obtained by use of a time-of-flight secondary ion mass spectrometer.
Figure 7D:
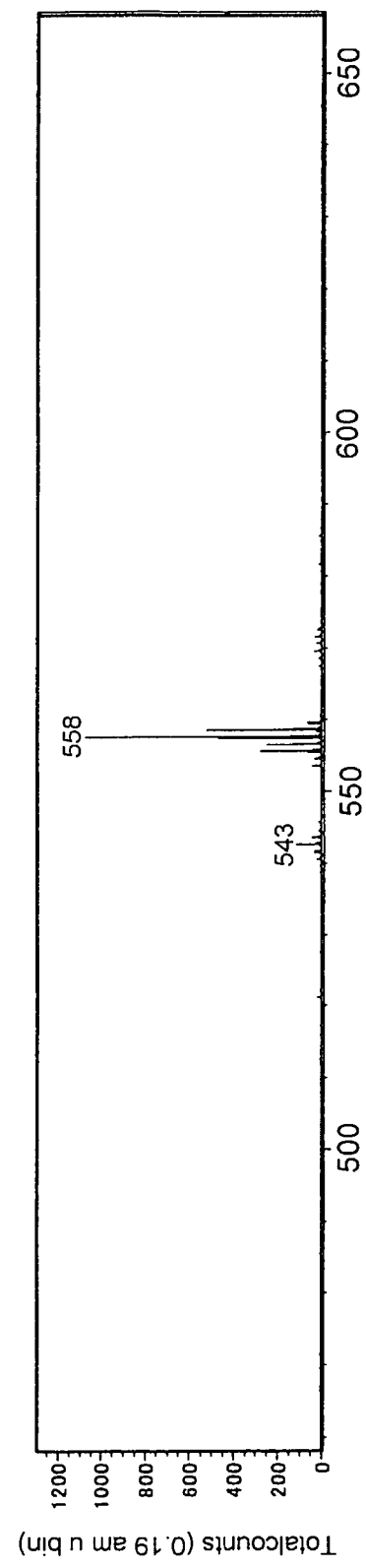
FIG. 7D shows a negative ion peak profile of a synthesized compound in Example 4 used for the present invention obtained by use of a time-of-flight secondary ion mass spectrometer.
Figure 8:
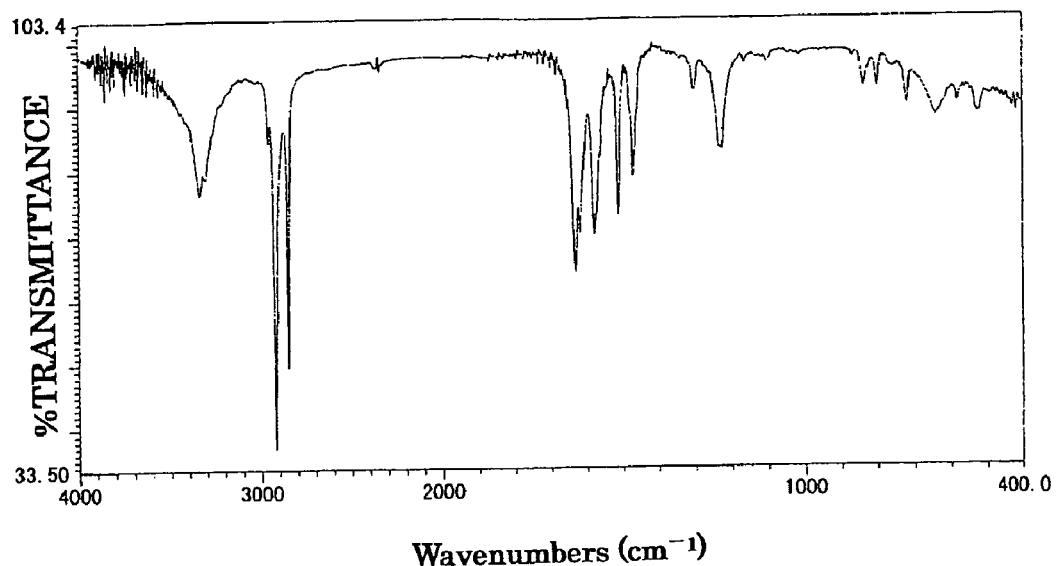
FIG. 8 shows an infrared absorption spectrum of a synthesized compound in Example 1 used for the present invention.
Figure 9:
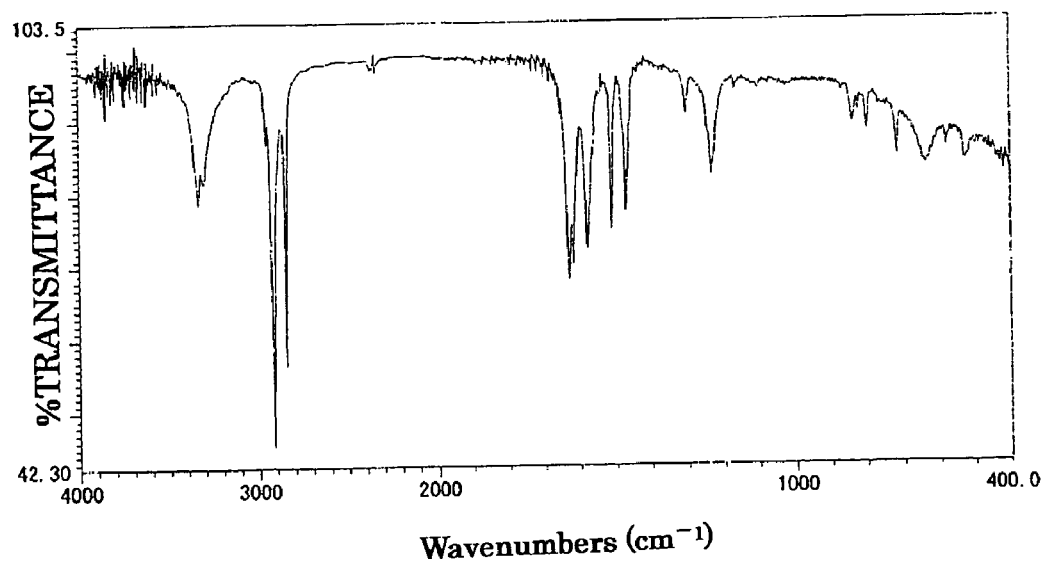
FIG. 9 shows an infrared absorption spectrum of a synthesized compound in Example 2 used for the present invention.
Figure 10:
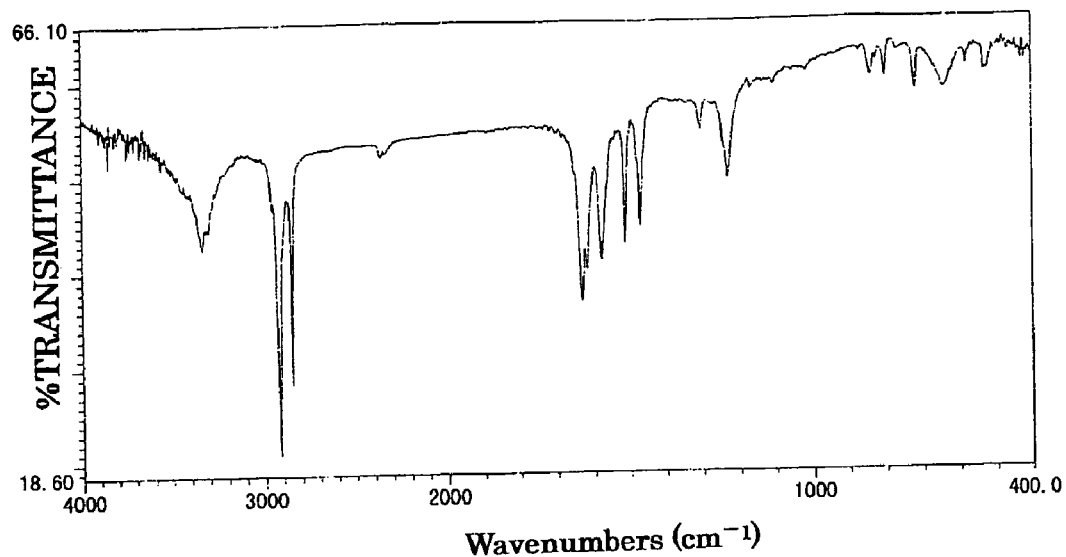
FIG. 10 shows an infrared absorption spectrum of a synthesized compound in Example 3 used for the present invention.
Figure 11:
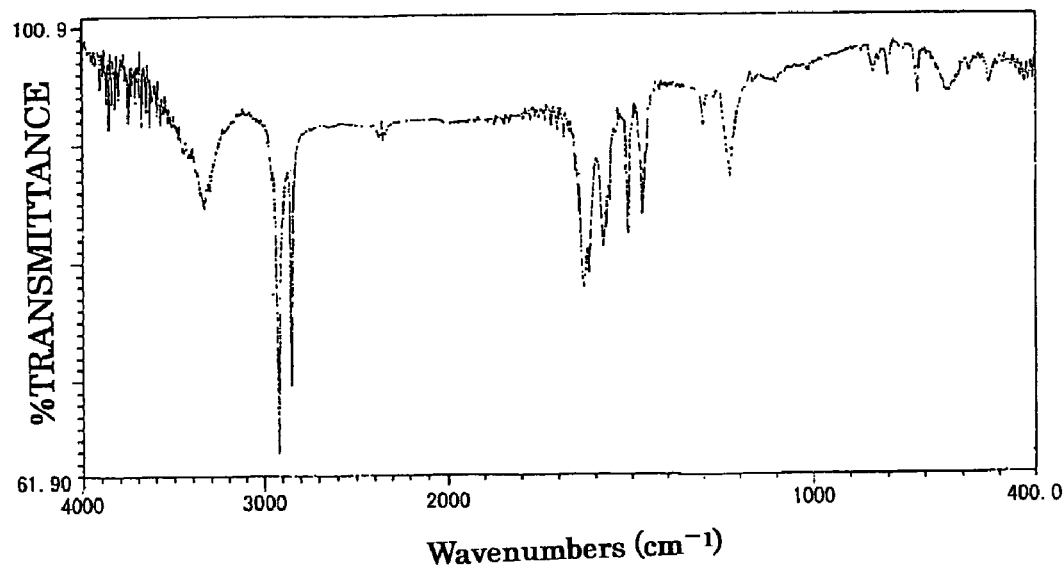
FIG. 11 shows an infrared absorption spectrum of a synthesized compound in Example 4 used for the present invention.
Figure 12:
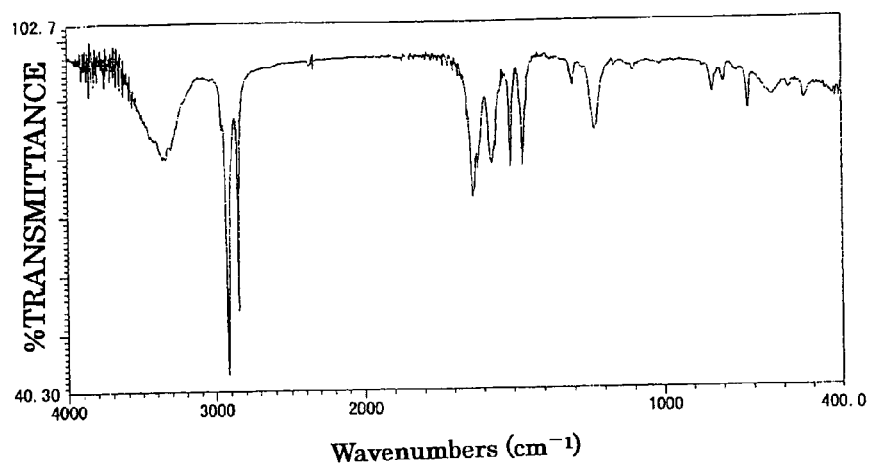
FIG. 12 shows an infrared absorption spectrum of a synthesized compound in Example 5 used for the present invention.

In the image-processing apparatus shown in FIG. 5B, the reversible thermosensitive recording medium 5, inserted from the entrance 30, progresses along the conveying root 50 shown by alternate long and short dash lines or alternatively progresses reversibly along the conveying root 50 in the apparatus. The reversible thermosensitive recording medium 5, inserted from the entrance 30, is conveyed in the apparatus by means of the conveying roller 31 and the guide roller 32. When it reaches the predetermined position on the conveying root 50, its existence is detected by means of sensor 33 and control unit 34c, the magnetic thermosensitive layer is subjected to magnetic recording or erasing between the magnetic head 34 and the platen roller 35, then the reversible thermosensitive recording medium passes between the guide roller 36 and the conveying roller 37 and subsequently between the guide roller 39 and the conveying roller 40. The reversible thermosensitive recording medium 5 is then subjected to heat treatment for erasing images between the ceramic heater 38 which recognizes its existence by means of sensor 43 through the ceramic heater control unit 38c and platen roller 44, conveyed along the conveying root 50 by means of conveying rollers 45, 46 and 47, subjected to image forming between thermal head 53 which recognizes its existence at a predetermined position by means of sensor 51 through the thermal head control unit 53c and platen roller 52 and discharged out of the apparatus from conveying root 56a through exit 61 by means of conveying roller 59 and guide roller 60. By the way, the temperature of ceramic heater 38 may be properly set depending on the application as explained earlier; the ceramic heater 38 is preferably set at 110° C. or more, more preferably 112° C. or more and most preferably 115° C. or more.

If desired, the reversible thermosensitive recording medium 5 may be directed to conveying root 56b by switching the conveying root changing unit 55a for another heat treatment between thermal head 53 and platen roller 52 by means of conveying belt 58 which moves reversibly by the action of limit switch 57a which operates by pressure of the reversible thermosensitive recording medium 5. Then the reversible thermosensitive recording medium 5 is conveyed through conveying root 49b, limit switch 57b and conveying belt 48 which are being connected by changing the conveying root changing unit 55b and discharged out of the apparatus from conveying root 56a through exit 61 by means of conveying roller 59 and guide roller 60. Further, such branched conveying root and conveying root changing unit may be placed on both sides of the ceramic heater 38. In this case, sensor 43a is preferably placed between platen roller 44 and conveying roller 45.

EXAMPLE

Herein below, with referring to Examples and Comparative Examples, the invention is explained in detail and the following Examples and Comparative Examples should not be construed as limiting the scope of this invention. All parts and percentages (%) are expressed by mass unless indicated otherwise.

Example 1

A Synthetic Example of Color Developer Expressed by Following Structural Formula

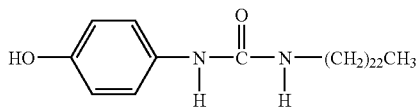

First, 200 mL of toluene and 13.3 g of lignoceric acid were added to a reaction container and 8.6 g of thionyl chloride was further added and heated to reflux for 8 hours. The solvent and thionyl chloride were distilled away under reduced pressure using an evaporator. 100 mL of acetone was added to the obtained acid chloride compound and stirred with ice application. An aqueous solution into which 3.5 g of sodium azide was melted was gradually added not to exceed a temperature of 10° C. and further stirred for 2 hours. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 3.5 g of p-aminophenol was added to the reaction solution, heat stirred for 1 hour, returned to a room temperature, precipitates were separated by filteration and it was washed with acetone. After drying, a compound was obtained by performing recrystallization using tetrahydrofran. The yield point was 15.2 g and the yield constant was 89%.

Example 2

A Synthetic Example of Color Developer Expressed by Following Structural Formula

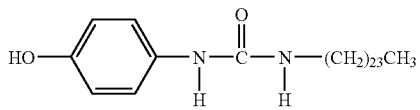

First, 100 mL of toluene and 5.4 g of pentacosanoic acid were added to a reaction container and 3.4 g of thionyl chloride was further added and heated to reflux for 6 hours. The solvent and thionyl chloride were distilled away under reduced pressure using an evaporator. 150 mL of acetone was added to the obtained acid chloride compound and stirred with ice application. An aqueous solution into which 1.4 g of sodium azide was melted was gradually added not to exceed a temperature of 10° C. and further stirred for 1 hour. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 1.5 g of p-aminophenol was added to the reaction solution, heat stirred for 1 hour, returned to a room temperature, precipitates were separated by filteration and it was washed with acetone. After drying, a compound was obtained by performing recrystallization using tetrahydrofran. The yield point was 5.8 g and the yield constant was 84%.

Example 3

A Synthetic Example of Color Developer Expressed by Following Structural Formula

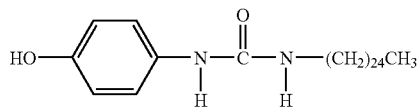

First, 250 mL of toluene and 12.0 g of cerinic acid were added to a reaction container and 7.2 g of thionyl chloride and a few drops of DMF were further added and heated to reflux for 8 hours. The solvent and thionyl chloride were distilled away under reduced pressure using an evaporator. 100 mL of acetone was added to the obtained acid chloride compound and stirred with ice application. An aqueous solution into which 2.9 g of sodium azide was melted was gradually added not to exceed a temperature of 10° C. and further stirred for 3 hours. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 3.3 g of p-aminophenol was added to the reaction solution, heat stirred for 1 hour, returned to a room temperature, precipitates were separated by filteration and it was washed with acetone. After drying, a compound was obtained by performing recrystallization using tetrahydrofran. The yield point was 11.4 g and the yield constant was 75%. The melting point was 143° C.

Example 4

A Synthetic Example of Color Developer Expressed by Following Structural Formula

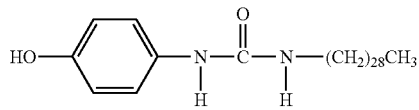

First, 50 mL of toluene and 2.0 g of melissic acid were added to a reaction container and 1.1 g of thionyl chloride and a few drops of DMF were further added and heated to reflux for 3 hours. The solvent and thionyl chloride were distilled away under reduced pressure using an evaporator. 10 mL of acetone was added to the obtained acid chloride compound and stirred with ice application. An aqueous solution into which 0.43 g of sodium azide was melted was gradually added not to exceed a temperature of 10° C. and further stirred for 1 and half hour. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 0.48 g of p-aminophenol was added to the reaction solution, heat stirred for 1 hour, returned to a room temperature, precipitates were separated by filteration and it was washed with acetone. After drying, a compound was obtained by performing recrystallization using tetrahydrofran. The yield point was 2.35 g and the yield constant was 95%.

Example 5

A Synthetic Example of Color Developer Expressed by Following Structural Formula

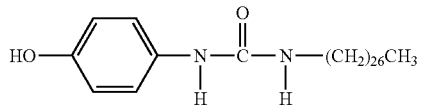

First, 350 mL of toluene and 10.5 g of montanic acid were added to a reaction container and 5.9 g of thionyl chloride and a few drops of DMF were further added and heated to reflux for 5 hours. The solvent and thionyl chloride were distilled away under reduced pressure using an evaporator. 300 mL of acetone was added to the obtained acid chloride compound and stirred with ice application. An aqueous solution into which 2.4 g of sodium azide was melted was gradually added not to exceed a temperature of 10° C. and further stirred for 1 hour. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 2.7 g of p-aminophenol was added to the reaction solution, heat stirred for 1 hour, returned to a room temperature, precipitates were separated by filteration and it was washed with acetone. After drying, a compound was obtained by performing recrystallization using tetrahydrofran. The yield point was 11.9 g and the yield constant was 91%.

Synthetic Example 1

A Synthetic Example of Color Developer Expressed by Following Structural Formula

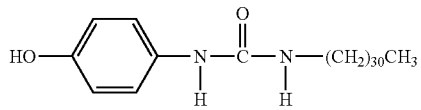

First, 200 mL of toluene and 4.5 g of dotria contanoic acid were added to a reaction container and 2.3 g of thionyl chloride and a few drops of DMF were further added and heated to reflux for 7 hours. The solvent and thionyl chloride were distilled away under reduced pressure using an evaporator. 200 mL of acetone was added to the obtained acid chloride compound and stirred with ice application. An aqueous solution into which 0.91 g of sodium azide was melted was gradually added not to exceed a temperature of 10° C. and further stirred for 3 hours. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 1.02 g of p-aminophenol was added to the reaction solution, heat stirred for 2 hours, returned to a room temperature, precipitates were separated by filteration and it was washed with acetone. After drying, a compound was obtained by performing recrystallization using tetrahydrofran. The yield point was 5.2 g and the yield constant was 95%.

Synthetic Example 2

A Synthetic Example of Color Developer Expressed by Following Structural Formula

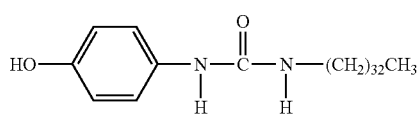

First, 200 mL of toluene and 4.6 g of tetratria contanoic acid were added to a reaction container and 2.2 g of thionyl chloride and a few drops of DMF were further added and heated to reflux for 7 hours. The solvent and thionyl chloride were distilled away under reduced pressure using an evaporator. 200 mL of acetone was added to the obtained acid chloride compound and stirred with ice application. An aqueous solution into which 0.88 g of sodium azide was melted was gradually added not to exceed a temperature of 10° C. and further stirred for 3 hours. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 0.99 g of p-aminophenol was added to the reaction solution, heat stirred for 2 hours, returned to a room temperature, precipitates were separated by filteration and it was washed with acetone. After drying, a compound was obtained by performing recrystallization using tetrahydrofran. The yield point was 5.1 g and the yield constant was 92%.

Synthetic Example 3

A Synthetic Example of Color Developer Expressed by Following Structural Formula

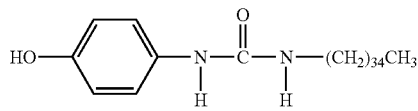

First, 200 mL of toluene and 5.1 g of hexatria contanoic acid were added to a reaction container and 2.2 g of thionyl chloride and a few drops of DMF were further added and heated to reflux for 7 hours. The solvent and thionyl chloride were distilled away under reduced pressure using an evaporator. 200 mL of acetone was added to the obtained acid chloride compound and stirred with ice application. An aqueous solution into which 0.93 g of sodium azide was melted was gradually added not to exceed a temperature of 10° C. and further stirred for 3 hours. The obtained reaction solution was extracted with toluene and washed and after it was dried with magnesium sulfate and transferred to the reaction solution, it was then heated at 80° C. of inner temperature. After nitrogen generation was completed and generation of isocyanate compound was confirmed, 1.04 g of p-aminophenol was added to the reaction solution, heat stirred for 2 hours, returned to a room temperature, precipitates were separated by filteration and it was washed with acetone. After drying, a compound was obtained by performing recrystallization using tetrahydrofran. The yield point was 5.9 g and the yield constant was 97%.

Identification and mass analysis of these compounds were conducted by TOF-SIMS (time-of-flight secondary ion mass spectrometer) using TRIFT III by Physical Electronics. Results are shown in Table 1. Furthermore, observed positive and negative peaks are shown in FIGS. 6A to 6H and 7A to 7H. Additionally, infrared absorption spectrums of Examples 1 to 5 are shown in FIGS. 8 to 12. Meanwhile, similar urea group-derived oscillation was observed in Synthetic Examples 1 to 3. From these results, it was confirmed that the aimed compounds expressed by Structural Formulae were obtained.

TABLE 1

| | Composition Formula | Melting Point | Molecular Mass Theory | Positive Peak Actual Measurement | Negative Peak Actual Measurement |
|---|---|---|---|---|---|
| Example 1 | $C_{30}H_{54}N_2O_2$ | 145° C. | 474.42 | 475 | 473 |
| Example 2 | $C_{31}H_{56}N_2O_2$ | 146° C. | 488.43 | 489 | 487 |
| Example 3 | $C_{32}H_{58}N_2O_2$ | 143° C. | 502.45 | 503 | 501 |
| Example 4 | $C_{36}H_{66}N_2O_2$ | 144° C. | 558.51 | 560 | 558 |
| Example 5 | $C_{34}H_{62}N_2O_2$ | 143° C. | 530.48 | 531 | 529 |
| Synthetic Example 1 | $C_{38}H_{70}N_2O_2$ | 142° C. | 586.54 | 588 | 586 |
| Synthetic Example 2 | $C_{40}H_{74}N_2O_2$ | 141° C. | 614.58 | 616 | 614 |
| Synthetic Example 3 | $C_{42}H_{78}N_2O_2$ | 139° C. | 642.61 | 644 | 642 |

Example 6

[Preparation of Thermosensitive Recording Layer]
color developer with a melting point of 145° C. expressed by following Structural Formula of Example 1 . . . 4 parts

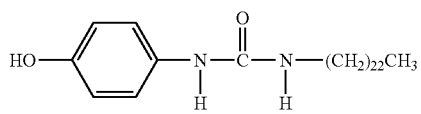

acrylpolyol resin (LR257 manufactured by Mitsubishi Rayon Co., Ltd., Solid content 50% solution, Hydroxy value 107) . . . 9 parts
methyl ethyl ketone . . . 70 parts The above-mentioned composition was pulverized and dispersed by means of a ball mill to approximately 1 μm of average particle diameter. To the resulting dispersion, 1.5 parts of 2-anilino-3-methyl-6-dibutylaminofluoran and 2 parts of adduct-type hexamethylenediisocyanate 75% solution in ethyl acetate (Colonate HL, manufactured by Nippon Polyurethane Industry Co., Ltd) was added and mixed well to prepare a coating liquid for thermosensitive recording layer.

Then the coating liquid for thermosensitive recording layer having the above-mentioned composition was applied on a white PET of 188 μm thickness by means of a wire bar, dried at 100° C. for 2 minutes, followed by heating at 60° C. for 24 hours, thereby a recording layer of about 11.0 μm thickness was provided.

[Preparation of Protective Layer]
40% solution of ultraviolet-absorbing polymer (UV-G300, manufactured by Nippon Shokubai Co., Ltd.) . . . 10 parts
isocyanate compound cross-linking agent (Colonate HX, manufactured by Nippon Polyurethane Industry Co., Ltd.) . . . 1.4 parts
silicone acrylic resin (GS-1015, manufactured by Toagosei Co., Ltd.) . . . 0.5 parts
methyl ethyl ketone . . . 10 parts The above-mentioned composition was mixed well to prepare a coating liquid for protective layer.

The coating liquid for protective layer having the above-mentioned composition was applied on the above-noted recording layer by means of a wire bar and dried at 100° C. for 2 minutes, followed by heating at 60° C. for 24 hours, thereby a protective layer of 3.5 μm thickness was provided. As a result, the reversible thermosensitive recording medium according to the present invention was prepared.

Example 7

A reversible thermosensitive recording medium was prepared in the same manner with Example 6, except for using the compound with the melting point of 146° C. expressed by following Structural Formula of Example 2 instead of the color developer used in Example 6.

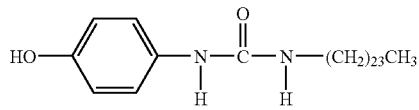

Example 8

A reversible thermosensitive recording medium was prepared in the same manner with Example 6, except for using the compound with the melting point of 143° C. expressed by following Structural Formula of Example 3 instead of the color developer used in Example 6.

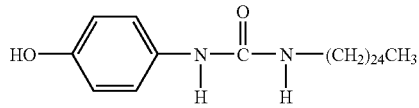

Example 9

A reversible thermosensitive recording medium was prepared in the same manner with Example 6, except for using the compound with the melting point of 143° C. expressed by following Structural Formula of Example 5 instead of the color developer used in Example 6.

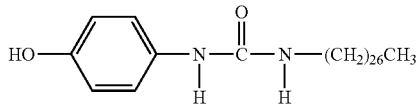

Example 10

A reversible thermosensitive recording medium was prepared in the same manner with Example 6, except for using the compound with the melting point of 144° C. expressed by following Structural Formula of Example 4 instead of the color developer used in Example 6.

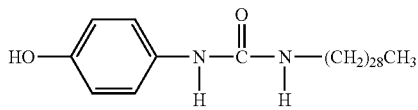

Example 11

A reversible thermosensitive recording medium was prepared in the same manner with Example 6, except for using the compound with the melting point of 142° C. expressed by following Structural Formula of Synthetic Example 1 instead of the color developer used in Example 6.

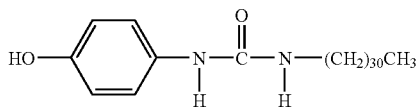

Example 12

A reversible thermosensitive recording medium was prepared in the same manner with Example 6, except for using the compound with the melting point of 141° C. expressed by following Structural Formula of Synthetic Example 2 instead of the color developer used in Example 6.

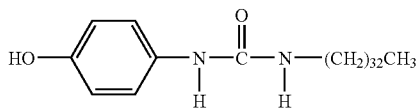

Example 13

A reversible thermosensitive recording medium was prepared in the same manner with Example 6, except for using the compound with the melting point of 139° C. expressed by following Structural Formula of Synthetic Example 3 instead of the color developer used in Example 6.

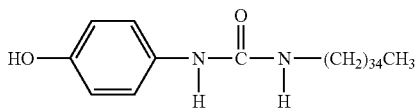

Example 14

A reversible thermosensitive recording medium of the present invention was prepared by disposing an intermediate layer and a protective layer on the recording layer prepared in Example 9.

[Preparation of Intermediate Layer]
    zinc oxide fine particle (ZS303 manufactured by Sumitomo Osaka Cement Co., Ltd.) . . . 4 parts
    heat-curable resin (LR257 manufactured by Mitsubishi Rayon Co., Ltd., Hydroxy value 107) . . . 2 parts
    Colonate HL . . . 0.5 parts methyl ethyl ketone . . . 4 parts The above composition was well stirred to prepare a coating liquid for intermediate layer. The coating liquid for intermediate layer was then applied on the recording layer prepared in Example 9 using a wire bar and dried at 100° C. for 2 minutes to form an intermediate layer of approximately 1.5 μm.

[Preparation of Protective Layer]
    urethane acrylate-based ultraviolet-curable resin (C7-157 manufactured by Dainippon Ink And Chemicals, Inc.) . . . 15 parts
    ethyl acetate . . . 85 parts The above composition was well melted and stirred to prepare a coating liquid for protective layer. The coating liquid for protective layer was then applied on the intermediate layer using a wire bar, dried at 90° C. for 1 minute and cured by passing below the ultraviolet lamp having irradiation energy of 80 W/cm at a transporting speed of 9 m/min. to form a protective layer of 3 μm thickness and a reversible thermosensitive recording medium of the present invention was prepared.

Comparative Example 1

A reversible thermosensitive recording medium was prepared in the same manner with Example 6, except for using the compound with the melting point of 145° C. expressed by following Structural Formula instead of the color developer used in Example 6.

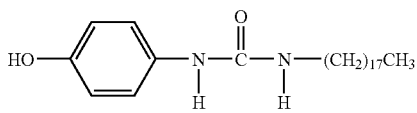

Comparative Example 2

A reversible thermosensitive recording medium was prepared in the same manner with Example 6, except for using the compound with the melting point of 145° C. expressed by following Structural Formula instead of the color developer used in Example 6.

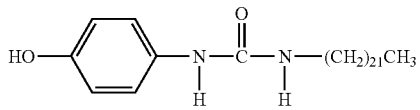

Comparative Example 3

A reversible thermosensitive recording medium was prepared in the same manner with Example 6, except for using the compound with the melting point of 171° C. expressed by following Structural Formula instead of the color developer used in Example 6.

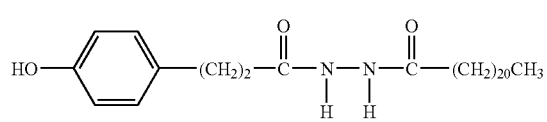

Comparative Example 4

A reversible thermosensitive recording medium was prepared in the same manner with Example 6, except for using the compound with the melting point of 173° C. expressed by following Structural Formula instead of the color developer used in Example 6.

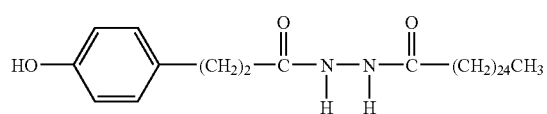

Comparative Example 5

A reversible thermosensitive recording medium was prepared in the same manner with Example 6, except for using the compound with the melting point of 118° C. expressed by following Structural Formula instead of the color developer used in Example 6.

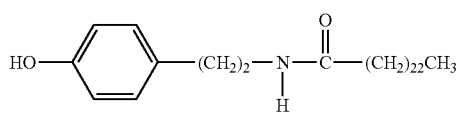

Thus prepared reversible thermosensitive recording media were subjected to the following test.

<Test 1: Coloring Property>

Printing was carried out by means of a thermosensitive printing simulator manufactured by Becom Co., Ltd. at the voltage described in Table 2 with a pulse width of 2 msec. Color optical density and background optical density were measured by means of Macbeth Densitometer RD914. The results are shown in Table 2.

TABLE 2

|  | Color Optical Density | | | Background Optical Density |
|---|---|---|---|---|
|  | 14 V | 16 V | 18 V |  |
| Example 6 | 0.40 | 1.14 | 1.51 | 0.09 |
| Example 7 | 0.48 | 1.42 | 1.79 | 0.09 |
| Example 8 | 0.46 | 1.39 | 1.54 | 0.09 |
| Example 9 | 0.51 | 1.40 | 1.64 | 0.09 |
| Example 10 | 0.51 | 1.35 | 1.57 | 0.09 |
| Example 11 | 0.46 | 1.34 | 1.65 | 0.10 |
| Example 12 | 0.53 | 1.37 | 1.58 | 0.10 |
| Example 13 | 0.55 | 1.41 | 1.57 | 0.10 |
| Example 14 | 0.46 | 1.39 | 1.62 | 0.09 |
| Comp. Example 1 | 0.31 | 1.16 | 1.58 | 0.10 |
| Comp. Example 2 | 0.48 | 1.14 | 1.70 | 0.10 |
| Comp. Example 3 | 0.19 | 0.52 | 0.95 | 0.10 |
| Comp. Example 4 | 0.18 | 0.49 | 0.94 | 0.10 |
| Comp. Example 5 | 0.58 | 1.26 | 1.28 | 0.10 |

<Test 2: Erasing Property>

As in test 1, printing was carried out by means of the thermosensitive printing apparatus manufactured by Becom Corp. at the voltage described in Table 3, heated by means of a heat slope tester manufactured by Toyo Seiki Kogyo Co., Ltd. for 1 second at 1 kgf/cm$^2$, and then the density before and after erasing was measured in the same way as in Test 1.

Note that the voltage during printing was suitably selected corresponding to the coloring sensitivity of the recording medium. The results are shown in Table 3.

TABLE 3

|  | Printing Voltage | Image Density | Erasing Temperature | Erasing Optical Density |
|---|---|---|---|---|
| Example 6 | 17 V | 1.50 | 130° C. | 0.10 |
| Example 7 | 17 V | 1.54 | 130° C. | 0.09 |
| Example 8 | 17 V | 1.48 | 130° C. | 0.09 |
| Example 9 | 17 V | 1.54 | 130° C. | 0.09 |
| Example 10 | 17 V | 1.50 | 130° C. | 0.09 |
| Example 11 | 17 V | 1.55 | 130° C. | 0.10 |
| Example 12 | 17 V | 1.48 | 130° C. | 0.10 |
| Example 13 | 17 V | 1.47 | 130° C. | 0.10 |
| Example 14 | 17 V | 1.42 | 130° C. | 0.09 |
| Comp. Example 1 | 17 V | 1.52 | 130° C. | 0.13 |
| Comp. Example 2 | 17 V | 1.52 | 130° C. | 0.11 |
| Comp. Example 3 | 19 V | 1.02 | 150° C. | 0.11 |
| Comp. Example 4 | 19 V | 1.03 | 150° C. | 0.11 |
| Comp. Example 5 | 15 V | 1.28 | 110° C. | 0.13 |

<Test 3: Erasing Property of Thermal Head>

As in test 2, printing was carried out by means of the thermosensitive printing apparatus manufactured by Becom Corp. and erasing was performed with energy of 9V to 17V in 0.5V intervals again on the printed image and the image density of the most erased parts was measured as in test 1. The erasing ratio of thermal head was calculated by the following formula.

Results are Shown in Table 4.

Erasing ratio of thermal head (%)=(1−(image density after erasing−background optical density)/(image density before erasing−background optical density))×100

TABLE 4

| | Erasing Ratio of Thermal Head |
|---|---|
| Example 6 | 80% |
| Example 7 | 83% |
| Example 8 | 82% |
| Example 9 | 84% |
| Example 10 | 83% |
| Example 11 | 84% |
| Example 12 | 83% |
| Example 13 | 82% |
| Example 14 | 85% |
| Comp. Example 1 | 56% |
| Comp. Example 2 | 70% |
| Comp. Example 3 | 76% |
| Comp. Example 4 | 78% |
| Comp. Example 5 | 21% |

<Test 4: Durability Test>

A durability test was conducted with 100 times of repeated printing and erasing using Card Reader/Writer manufactured by Panasonic Communications Co., Ltd. The printing was performed with energy by which color optical density of each reversible thermosensitive recording medium reaches a practical density of 1.2 or more or a saturated density when the density is less than 1.2. The erasing was performed at an erasing temperature at which the density of erasing residue becomes the least. The image density, erasing optical density and background optical density of the first and 100$^{th}$ time were measured with the same manner as in Test 1 and the density of erasing residue was calculated by the following formula.

Density of erasing residue=erasing optical density−background optical density

Moreover, the surface condition of each recording medium after the test was visually evaluated. The results are shown in Table 5.

TABLE 5

| | 1st Time | | 100th Time | | Surface |
|---|---|---|---|---|---|
| | Image Density | Erasing Residue Density | Image Density | Erasing Residue Density | Condition of Recording Medium |
| Example 6 | 1.23 | 0.00 | 1.20 | 0.01 | no striking mark |
| Example 7 | 1.24 | 0.00 | 1.21 | 0.01 | no striking mark |
| Example 8 | 1.23 | 0.00 | 1.22 | 0.00 | no striking mark |
| Example 9 | 1.25 | 0.00 | 1.23 | 0.00 | no striking mark |
| Example 10 | 1.24 | 0.00 | 1.22 | 0.00 | no striking mark |
| Example 11 | 1.23 | 0.00 | 1.21 | 0.00 | no striking mark |
| Example 12 | 1.23 | 0.00 | 1.22 | 0.00 | no striking mark |
| Example 13 | 1.24 | 0.00 | 1.22 | 0.01 | no striking mark |
| Example 14 | 1.26 | 0.00 | 1.24 | 0.00 | no striking mark |
| Comp. Example 1 | 1.24 | 0.03 | 1.22 | 0.07 | no striking mark |
| Comp. Example 2 | 1.22 | 0.02 | 1.20 | 0.05 | no striking mark |
| Comp. Example 3 | 1.10 | 0.00 | 0.98 | 0.04 | striking mark in printed part |
| Comp. Example 4 | 1.12 | 0.00 | 0.96 | 0.05 | striking mark in printed part |
| Comp. Example 5 | 1.26 | 0.03 | 1.21 | 0.07 | no striking mark |

<Test 5: Image Preservability>

Printed image obtained in Test 2 was preserved for 24 hours under dry conditions of 50° C., 60° C. and 70° C. Densities before and after preservation were measured in the same way as in Test 1 and image retention rate was calculated according to the following equation. The results are shown in Table 6.

Image retention rate (%)=(image density after preservation−background optical density after preservation)/(image density before preservation−background optical density before preservation)×100

TABLE 6

| | Image Preservability (50° C.) | Image Preservability (60° C.) | Image Preservability (70° C.) |
|---|---|---|---|
| Example 6 | 96% | 81% | 11% |
| Example 7 | 96% | 90% | 10% |
| Example 8 | 98% | 95% | 16% |
| Example 9 | 98% | 96% | 82% |
| Example 10 | 98% | 96% | 91% |
| Example 11 | 98% | 96% | 96% |
| Example 12 | 98% | 96% | 97% |
| Example 13 | 98% | 96% | 98% |
| Example 14 | 99% | 95% | 85% |
| Comp. Example 1 | 8% | 6% | 1% |
| Comp. Example 2 | 86% | 16% | 3% |
| Comp. Example 3 | 85% | 59% | 9% |
| Comp. Example 4 | 88% | 61% | 12% |
| Comp. Example 5 | 88% | 43% | 7% |

<Test 6: Color Optical Density Change Relative to Temperature>

The printed image obtained in Test 2 was cut into pieces of 0.5 cm×0.5 cm; applied on a hot plate with the temperature increasing by 3° C./min and heated at 30° C. to 140° C. The color optical density change associated with the temperature change was measured using Macbeth Densitometer RD914. The measurement results are shown in FIG. 13.

Figure 13:
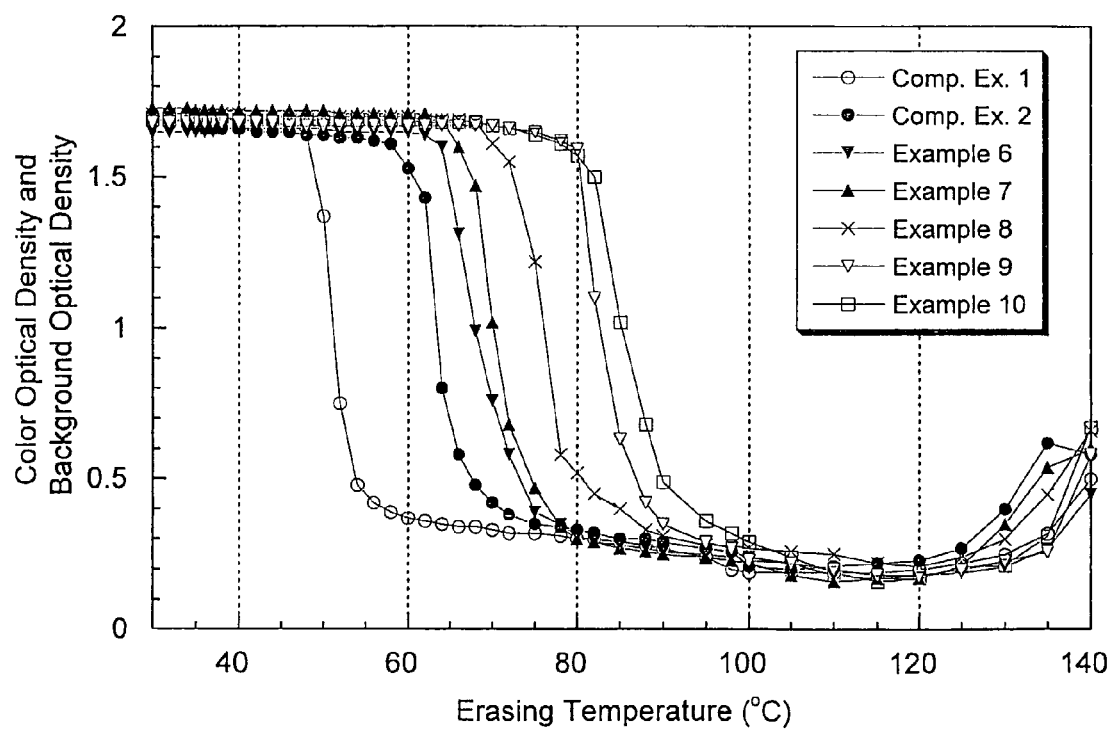
FIG. 13 shows a color optical density change based on the temperature of the reversible thermosensitive coloring composition employing the present invention.

As shown in FIG. 13, erasing was started at approximately 40° C. in Comparative Example 1 in which a compound having alkyl group of carbon number 18 and urea group is used and the erasing was started at 60° C. or less in Comparative Example 2 in which a compound having alkyl group of carbon number 22 and urea group is used. On the other hand, the color optical densities of the reversible thermosensitive recording media using the compound of the present invention having alkyl group of carbon number 23 or more and urea group are not deteriorated even at 60° C. or more.

As regard to the above results as shown in Table 2, Examples of the present invention exhibit high density at low energy as compared with Comparative Examples 3 and 4 which have high melting points and the difference is apparently notable in color optical density.

And as shown in Tables 3 and 4, the erasing properties of Examples of the present invention are appropriate and it turns out that they are favorable for high-speed erasing.

Next, as shown in Table 5, Examples of the present invention exhibit no deterioration of image density by repetition or no occurrence of erasing residue and it turns out that they have distinctly appropriate durability with no striking marks in the surface of the recording media.

Furthermore, as shown in Table 6, Examples exhibit high image preservability. On the other hand, in Comparative Examples, the image retention rates at 60° C. in a dried condition are deteriorated and in particular, Comparative Examples 1 and 2 exhibit notable deterioration of the density.

As it is apparent from above results, the reversible thermosensitive recording medium of the present invention in which a compound having alkyl group of carbon number 23 or more and urea group is used as color developer is highly practical for use because of high coloring sensitivity, appropriate high-speed erasing ability and excellent repeated durability and image preservability.

INDUSTRIAL APPLICABILITY

The reversible thermosensitive recording medium of the present invention is applied for prepaid card, point card and also credit card, when formed into a card-like shape. The recording medium formed into a sheet-like shape may be applied for normal document, instructing letter for process management, or the like, owing to wider printable area than the card-like size. Accordingly, the reversible thermosensitive recording medium of the present invention may be applied in a wide range of stickers, e.g. on an entry/exit ticket, container for frozen foods, industrial product, various chemical container; and applied for large screens or various displays, e.g. for physical distribution management, production process management.

The invention claimed is:

1. A reversible thermosensitive recording medium comprising:
a support; and
a thermosensitive recording layer formed on the support,
wherein the thermosensitive recording layer comprises an electron-donating coloring compound and an electron-accepting compound,
the thermosensitive recording layer is capable of forming a relatively developed condition and a relatively erased condition depending on at least one of the difference of heating temperatures and the difference of cooling rates following to heating, and
the electron-accepting compound comprises a phenol compound expressed by following General Formula (1):

General Formula (1)

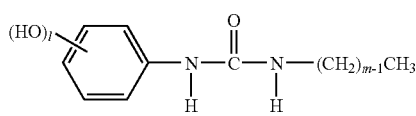

where, in the General Formula (1), "1" represents an integer of 1 to 3 and "m" represents an integer of 23 or more.

2. The reversible thermosensitive recording medium according to claim 1, wherein "m" represents an integer of 23 to 40.

3. The reversible thermosensitive recording medium according to claim 1, wherein the thermosensitive recording layer comprises a crosslinked resin.

4. The reversible thermosensitive recording medium according to claim 3, wherein the crosslinked resin has a hydroxyl value of 70 KO Hmg/g or more.

5. The reversible thermosensitive recording medium according to any one of claim 3, wherein the crosslinked resin is an acrylpolyol resin.

6. The reversible thermosensitive recording medium according to claim 3, wherein the crosslinked resin is crosslinked with an isocyanate compound.

7. The reversible thermosensitive recording medium according to claim 1, wherein the electron-donating coloring compound is a leuco dye.

8. The reversible thermosensitive recording medium according to claim 1, wherein the reversible thermosensitive recording medium comprises a protective layer on the thermosensitive recording layer and the protective layer comprises a crosslinked resin.

9. The reversible thermosensitive recording medium according to claim 8, wherein the protective layer comprises an ultraviolet-absorbing polymer.

10. The reversible thermosensitive recording medium according to claim 8, wherein the protective layer comprises ultraviolet-absorbing inorganic fine particles.

11. The reversible thermosensitive recording medium according to claim 1, wherein the reversible thermosensitive recording medium is formed into one of a card-like, label-like, sheet-like and roll-like configurations.

12. A reversible thermosensitive recording label comprising:
a reversible thermosensitive recording medium; and
one of an adhesive layer and a tacky layer,
wherein one of the adhesive layer and the tacky layer is disposed on a surface of the reversible thermosensitive recording medium opposite to the surface on which an image is formed,
wherein the reversible thermosensitive recording medium comprises
a support; and
a thermosensitive recording layer formed on the support,
wherein the thermosensitive recording layer comprises an electron-donating coloring compound and an electron-accepting compound,
the thermosensitive recording layer is capable of forming a relatively developed condition and a relatively erased condition depending on at least one of the difference of heating temperatures and the difference of cooling rates following heating, and
the electron-accepting compound comprises a phenol compound expressed by the following General Formula (2):

General Formula (2)

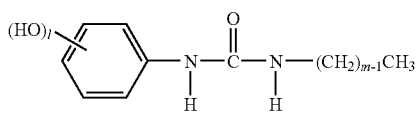

where, in the General Formula (2), "1" represents and integer of 1 to 3 and "m" represents an integer of 23 or more.

13. A reversible thermosensitive recording member comprising:
an information-memorizing part; and
a reversible displaying part,
wherein the reversible displaying part comprises the reversible thermosensitive recording medium which comprises:
a support; and
a thermosensitive recording layer formed on the support,
wherein the thermosensitive recording layer comprises an electron-donating coloring compound and an electron-accepting compound,
the thermosensitive recording layer is capable of forming a relatively developed condition and a relatively erased condition depending on at least one of the difference of heating temperatures and the difference of cooling rates following heating, and
the electron-accepting compound comprises a phenol compound expressed by following General Formula (3):

General Formula (3)

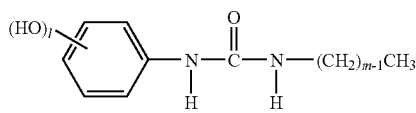

where, in the General Formula (3), "1" represents an integer of 1 to 3 and "m" represents an integer of 23 or more.

14. The reversible thermosensitive recording member according to claim 13, wherein the information-memorizing part and the reversible displaying part are integrated.

15. The reversible thermosensitive recording member according to claim 13, wherein the information-memorizing part is selected from a magnetic thermosensitive layer, a magnetic stripe, an IC memory, an optical memory, a hologram, a RF-ID tag card, a disc, a disc cartridge and a tape cassette.

16. An image-processing apparatus comprising:
an image-forming unit and/or an image-erasing unit,
wherein images are formed on a reversible thermosensitive recording medium by heating the reversible thermosensitive recording medium in the image-forming unit,
images are erased from the reversible thermosensitive recording medium by heating the reversible thermosensitive recording medium in the image-erasing unit, and
the reversible thermosensitive recording medium comprises:
a support; and
a thermosensitive recording layer formed on the support,
wherein the thermosensitive recording layer comprises an electron-donating coloring compound and an electron-accepting compound,
the thermosensitive recording layer is capable of forming a relatively developed condition and a relatively erased condition depending on at least one of the difference of heating temperatures and the difference of cooling rates following heating, and
the electron-accepting compound comprises a phenol compound expressed by the following General Formula (4):

General Formula (4)

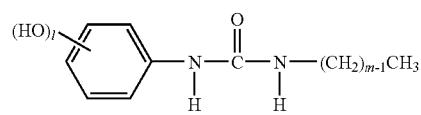

where, in the General Formula (4), "1" represents an integer of 1 to 3 and "m" represents an integer of 23 or more.

17. The image-processing apparatus according to claim 16, wherein the image-forming unit is a thermal head or a laser irradiation apparatus.

18. The image-processing apparatus according to claim 16, wherein the image-erasing unit is one selected from a thermal head, a ceramic heater, a heat roll, a hot stamp, a heat block and a laser irradiation apparatus.

19. An image-processing method comprising:
one of forming images on a reversible thermosensitive recording medium by heating the reversible thermosensitive recording medium, and
erasing the images from the reversible thermosensitive recording medium by heating the reversible thermosensitive recording medium,
wherein the reversible thermosensitive recording medium comprises:
a support; and
a thermosensitive recording layer formed on the support,
wherein the thermosensitive recording layer comprises an electron-donating coloring compound and an electron-accepting compound,
the thermosensitive recording layer is capable of forming a relatively developed condition and a relatively erased condition depending on at least one of the difference of heating temperatures and the difference of cooling rates following heating, and
the electron-accepting compound comprises a phenol compound expressed by the General Formula (5):

General Formula (5)

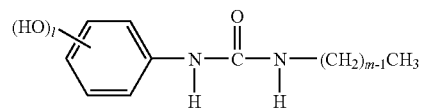

where, in the General Formula (5), "1" represents an integer of 1 to 3 and "m" represents an integer of 23 or more.

20. The image-processing method according to claim 19, wherein the images are formed with a means selected from a thermal head and a laser irradiation apparatus.

21. The image-processing method according to claim 19, wherein the images are erased with a means selected from a thermal head, a ceramic heater, a heat roll, a hot stamp, a heat block and a laser irradiation apparatus.

22. The image-processing method according to claim 19, wherein the image-processing method comprises forming new images while the old images are being erased with the thermal head.

23. A phenol compound comprising:
a structure expressed by following General Formula (6),

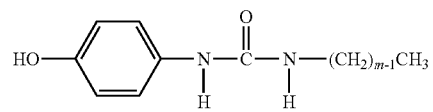

General Formula (6)

where, in the General Formula (6), "m" represents an integer of 23 to 29.

* * * * *